United States Patent
Tang et al.

(10) Patent No.: US 12,054,477 B2
(45) Date of Patent: Aug. 6, 2024

(54) PRODRUG OF PYRROLIDONE DERIVATIVES AS GLUCOKINASE ACTIVATOR

(71) Applicant: HUA MEDICINE (SHANGHAI) LTD., Shanghai (CN)

(72) Inventors: Fuxing Tang, Shanghai (CN); Jin She, Shanghai (CN); Li Chen, Shanghai (CN); Guanghua Lv, Shanghai (CN); Xiangle Jin, Shanghai (CN)

(73) Assignee: HUA MEDICINE (SHANGHAI) LTD., Shanghai (CN)

( * ) Notice: Subject to any disclaimer, the term of this patent is extended or adjusted under 35 U.S.C. 154(b) by 0 days.

(21) Appl. No.: 18/333,459

(22) Filed: Jun. 12, 2023

(65) Prior Publication Data
US 2023/0322738 A1   Oct. 12, 2023

Related U.S. Application Data

(63) Continuation of application No. PCT/CN2022/118947, filed on Sep. 15, 2022.

(30) Foreign Application Priority Data

Sep. 15, 2021 (CN) .......................... 202111079620.5
Sep. 8, 2022 (CN) .......................... 202211093895.9

(51) Int. Cl.
*C07D 403/12* (2006.01)
*A61P 3/10* (2006.01)
*C07D 401/14* (2006.01)
*C07D 405/14* (2006.01)

(52) U.S. Cl.
CPC .............. *C07D 403/12* (2013.01); *A61P 3/10* (2018.01); *C07D 401/14* (2013.01); *C07D 405/14* (2013.01)

(58) Field of Classification Search
CPC .................................................... C07D 403/12
See application file for complete search history.

(56) References Cited

U.S. PATENT DOCUMENTS

| | | |
|---|---|---|
| 8,772,541 B2 | 7/2014 | Xie et al. |
| 10,689,360 B1 | 6/2020 | Zavoronkovs et al. |
| 11,008,303 B2 | 5/2021 | Zavoronkovs et al. |
| 2003/0114435 A1 | 6/2003 | Tani et al. |
| 2019/0328713 A1 | 10/2019 | Chen et al. |

FOREIGN PATENT DOCUMENTS

| | | |
|---|---|---|
| EP | 3804716 A1 | 4/2021 |
| WO | WO 2002/000651 A3 | 6/2002 |
| WO | WO 2008/077507 A1 | 7/2008 |
| WO | WO 2009/126782 A1 | 10/2009 |
| WO | WO 2009/127544 A1 | 10/2009 |
| WO | WO 2009/127546 A1 | 10/2009 |
| WO | WO 2010/048149 A3 | 9/2010 |
| WO | WO 2010/075376 A3 | 9/2010 |
| WO | WO 2012/129562 A3 | 1/2013 |
| WO | WO 2017/004383 A1 | 1/2017 |
| WO | WO 2017/066705 A1 | 4/2017 |
| WO | WO 2018/195439 A3 | 11/2018 |
| WO | WO 2020/150417 A3 | 8/2020 |
| WO | WO 2022/040604 A1 | 2/2022 |

OTHER PUBLICATIONS

RN 1191999-68-4 of STN Registry in STNext., 2009.*
Wuts et al., "Protection for the hydroxyl group, including 1,2- and 1,3-diols", *Greene's Protective Groups in Organic Synthesis*, Fourth Edition, p. 16-366 (2007).
International Search Report and Written Opinion for International Application No. PCT/CN2022/118947, mailed Nov. 28, 2022.

* cited by examiner

Primary Examiner — Brian E McDowell
(74) Attorney, Agent, or Firm — Jones Day

(57) ABSTRACT

The present disclosure provides a compound of formula (I), or an isotopically labeled product, an enantiomer, a diastereomer or a pharmaceutically acceptable salt thereof; a pharmaceutical composition comprising a compound of formula (I); and use of a compound of formula (I) or a pharmaceutical composition thereof in the treatment of diabetes mellitus and related symptoms.

(I)

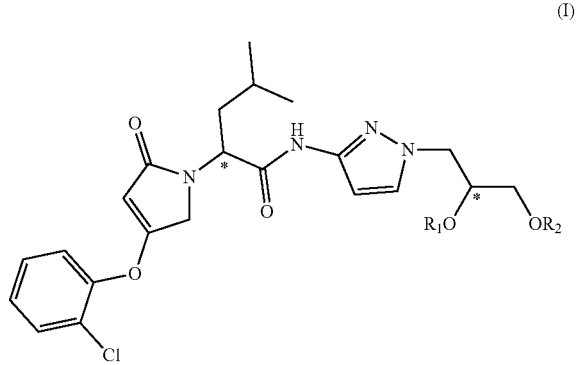

19 Claims, 4 Drawing Sheets

PRODRUG OF PYRROLIDONE DERIVATIVES AS GLUCOKINASE ACTIVATOR

CROSS REFERENCE TO RELATED APPLICATIONS

This application is a continuation application of International Patent Application No. PCT/CN2022/118947, filed on Sep. 15, 2022, which claims the priorities pursuant to 35 U.S.C. § 365(b) to Chinese Patent Application No. 202111079620.5 filed on Sep. 15, 2021, and Chinese Patent Application No. 202211093895.9 filed on Sep. 8, 2022, the entireties of each of which are incorporated herein by reference.

FIELD OF THE INVENTION

The present disclosure relates to prodrugs of pyrrolidone derivatives as glucokinase activator (GKA), pharmaceutical compositions thereof, and their use in the treatment of diabetes mellitus and related diseases. More specifically, the present disclosure relates to derivatives of HMS5552, pharmaceutical compositions comprising the same, and their use in the manufacture of medicaments for the treatment of diabetes mellitus and related diseases.

BACKGROUND OF THE INVENTION

Diabetes mellitus has become a prevalent disease worldwide. According to the data from the 24th National Conference of the Chinese Diabetes Society (CDS), China has the largest population of patients with diabetes worldwide, and about 129.8 million adults have diabetes. Type II diabetes, i.e., non-insulin dependent diabetes mellitus (NIDDM), which comprises of more than 90% of patients with diabetes, is a hyperglycemic chronic, metabolic dysfunction resulting from an imbalance of blood glucose homeostasis in human body caused by insulin secretion disorder and insulin resistance.

Glucokinase (GK) plays a central role in stabilizing blood glucose balance in human body. GK, which acts as a glucose sensor in blood glucose homeostasis, senses blood glucose changes, regulates the secretion of messenger glucose-controlling hormones, insulin, glucagon, and GLP-1, and constitutes a sensing system for regulation of blood glucose homeostasis in human body. GK is mainly distributed in the liver, where it rapidly converts glucose into hepatic glycogen for storage in response to elevated blood glucose, while lowering the glucose level in the blood. Glucose reserve during glucose ingestion and glucose supply during fasting, controlled by glucose-controlling hormones, constitute the regulation of blood glucose homeostasis in human body.

Impaired function and expression of glucokinase, and the dysfunction of the glucose sensor, result in the dysfunction of the early phase secretion of glucose-controlling hormones, affecting glucose uptake and output, and resulting in post-prandial hyperglycemia and pre-prandial hypoglycemia. Abnormal signaling of glucose-controlling hormones cause abnormal functions and expressions of key proteins in the execution system of glucose uptake and output, forming abnormal operating state, and leading to type II diabetes.

Glucokinase activators were developed against the characteristics of GK as a target, which can improve the secretion function of insulin, glucagon and GLP-1 for glucose regulation by increasing the sensitivity of α, β and L cells to changes in glucose concentration.

WO2009/127546A1 discloses glucokinase activators of pyrrolidone series, in particular, (S)-2-[4-(2-chloro-phenoxy)-2-oxo-2,5-dihydro-pyrrol-1-yl]-4-methyl-pentanoic acid [1-((R)-2,3-dihydroxy-propyl)-1H-pyrazol-3-yl]-amide, referred to as Dorzagliatin (or HMS5552).

In view of the important role of glucokinase activators in the regulation of blood glucose homeostasis in human body, there is a demand for glucokinase activators in this field.

SUMMARY OF THE INVENTION

The inventors of the present disclosure have developed a class of compounds, which are derivatives of HMS5552, can be efficiently converted (e.g., undergo enzymatic and/or chemical transformation) into HMS5552 in vivo (particularly in the small intestine), and thus are absorbed into the circulatory system to achieve the purpose of treating or preventing some metabolic syndrome diseases. Alternatively, the compounds disclosed herein are characterized in that it is stable in gastric fluid, and can be efficiently converted into HMS5552 in intestinal and small intestinal cells. In addition, the derivatives of HMS5552 disclosed herein have good physicochemical stability and solubility.

The present disclosure relates to a compound of formula (I), or an isotopically labeled product, an enantiomer, a diastereomer or a pharmaceutically acceptable salt thereof:

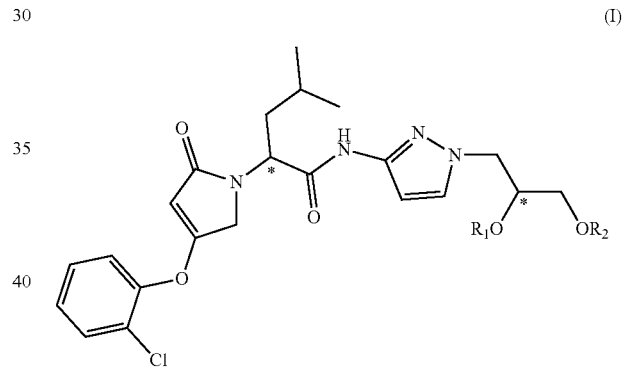

(I)

wherein
* indicates a chiral center,
$R_1$ is selected from H, —C(O)$R_6$, —C(O)O$R_6$, —C(O)N$R_7R_8$, —S(O)$_m R_6$, —S(O)$_m$O$R_6$, or —S(O)$_m$N$R_7R_8$;
$R_2$ is selected from —C(O)$R_3$, —C(O)O$R_3$, —C(O)N$R_4R_5$, —S(O)$_m R_3$, —S(O)$_m$O$R_3$, or —S(O)$_m$N$R_4R_5$;
or $R_1$ and $R_2$ are connected to form —CHR$_d$—, —SiR$_d R_e$—, —C(O)—, —S(O)$_{1-2}$—, —P(O)O$R_d$—, or —CR$_d R_e$—CR$_d R_e$—;
$R_3$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl, which is optionally substituted with 1, 2, 3, 4 or 5 R groups;
$R_4$ and $R_5$ are independently selected from H, $C_{1-6}$ alkyl, $C_{2-6}$ alkenyl, $C_{2-6}$ alkynyl, or $C_{1-6}$ haloalkyl; alternatively, $R_4$ and $R_5$ are taken together with the N atom to form 3- to 7-membered heterocyclyl;
$R_6$ is independently selected from H, $C_{1-6}$ alkyl, $C_{2-6}$ alkenyl, $C_{2-6}$ alkynyl, or $C_{1-6}$ haloalkyl;
$R_7$ and $R_8$ are independently selected from H, $C_{1-6}$ alkyl, $C_{2-6}$ alkenyl, $C_{2-6}$ alkynyl, or $C_{1-6}$ haloalkyl; alternatively, $R_7$ and $R_5$ are taken together with the N atom to form 3- to 7-membered heterocyclyl;

R is independently selected from H, -L-halogen, -L-CN, -L-NO$_2$, -L-OR$_a$, -L-SR$_a$, -L-NR$_b$R$_c$, -L-C(O)OR$_a$, -L-C(O)NR$_b$R$_c$, -L-S(O)$_m$OR$_a$, -L-S(O)$_m$NR$_b$R$_c$, C$_{1-6}$ alkyl, C$_{1-6}$ haloalkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, 5- to 10-membered heteroaryl, or a side chain of a natural amino acid;

wherein m is 1 or 2;

$R_a$ is independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, or 5- to 10-membered heteroaryl;

$R_b$ and $R_c$ are independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, or 5- to 10-membered heteroaryl; alternatively, $R_b$ and $R_c$ are taken together with the N atom to form 3- to 7-membered heterocyclyl;

$R_d$ and $R_e$ are independently selected from H, C$_{1-6}$ alkyl, C$_{2-6}$ alkenyl, C$_{2-6}$ alkynyl, or C$_{1-6}$ haloalkyl; alternatively, $R_d$ and $R_e$ are taken together with the C atom to form =O, =S, C$_{3-7}$ cycloalkyl, or 3- to 7-membered heterocyclyl;

L is selected from a chemical bond, —C$_{1-6}$ alkylene-, —C$_{2-6}$ alkenylene-, or —C$_{2-6}$ alkynylene-.

The present disclosure also relates to a pharmaceutical composition, comprising a therapeutically effective amount of a compound of the present disclosure, or an isotopically labeled product, an enantiomer, a diastereoisomer, or a pharmaceutically acceptable salt thereof; and optionally one or more pharmaceutically acceptable excipients.

The present disclosure also relates to a drug combination, comprising a therapeutically effective amount of a compound of the present disclosure, or an isotopically labeled product, an enantiomer, a diastereoisomer, or a pharmaceutically acceptable salt thereof, and at least one other glucose-lowering agent.

The present disclosure also relates to the use of a compound of the present disclosure, or an isotopically labeled product, an enantiomer, a diastereoisomer, or a pharmaceutically acceptable salt thereof, or a pharmaceutical composition of the present disclosure in the manufacture of a medicament for the treatment or prevention of one or more diseases selected from type I diabetes mellitus, type II diabetes mellitus, impaired glucose tolerance, impaired fasting blood glucose, hyperglycemia, postprandial hyperglycemia, overweight, obesity, hypertension, insulin resistance, and metabolic syndrome.

The present disclosure also relates to a compound of the present disclosure, or an isotopically labeled product, an enantiomer, a diastereoisomer, or a pharmaceutically acceptable salt thereof; or a pharmaceutical composition of the present disclosure, for use in the treatment or prevention of one or more diseases selected from type I diabetes mellitus, type II diabetes mellitus, impaired glucose tolerance, impaired fasting blood glucose, hyperglycemia, postprandial hyperglycemia, overweight, obesity, hypertension, insulin resistance, and metabolic syndrome.

The present disclosure also relates to a method for the treatment or prevention of one or more diseases selected from type I diabetes mellitus, type II diabetes mellitus, impaired glucose tolerance, impaired fasting blood glucose, hyperglycemia, postprandial hyperglycemia, overweight, obesity, hypertension, insulin resistance, and metabolic syndrome, comprising administering to a subject a compound of the present disclosure, or an isotopically labeled product, an enantiomer, a diastereoisomer, or a pharmaceutically acceptable salt thereof, or a pharmaceutical composition of the present disclosure.

The present disclosure also relates to the use of a compound of the present disclosure, or an isotopically labeled product, an enantiomer, a diastereoisomer, or a pharmaceutically acceptable salt thereof, or a pharmaceutical composition of the present disclosure in the manufacture of a medicament for curing diabetes, inducing remission or regression of diabetes.

The present disclosure also relates to a compound of the present disclosure, or an isotopically labeled product, an enantiomer, a diastereoisomer, or a pharmaceutically acceptable salt thereof, or a pharmaceutical composition of the present disclosure, for use of curing diabetes, inducing remission or regression of diabetes.

The present disclosure also relates to a method for curing diabetes, inducing remission or regression of diabetes, comprising administering to a subject a compound of the present disclosure, or an isotopically labeled product, an enantiomer, a diastereoisomer, or a pharmaceutically acceptable salt thereof; or a pharmaceutical composition of the present disclosure.

DETAILED DESCRIPTION OF THE INVENTION

Definitions

Unless otherwise specified, all technical and scientific terms used herein have the same meanings as commonly understood by those skilled in the art to which the present disclosure belongs, but in case of conflict, the definitions in this specification shall prevail.

As used in the specification and claims, the singular forms "a", "an" and "the (said)" include plural forms, unless clearly specified otherwise in the context.

All numerical values or expressions related to component amounts used in the specification and claims should be understood to be modified by "about" in all cases. The term "about" when referring to an amount or a numerical range means that the amount or the numerical range referred to is an approximate value within experimental variability (or within statistical experimental error). Therefore, the amount or the numerical range can be varied between, for example, ±5% of the amount or the numerical range referred to.

When a range of values is listed, it is intended to encompass each value and sub-range within the range. For example, "C$_{1-6}$ alkyl" is intended to include C$_1$, C$_2$, C$_3$, C$_4$, C$_5$, C$_6$, C$_{1-6}$, C$_{1-5}$, C$_{1-4}$, C$_{1-3}$, C$_{1-2}$, C$_{2-6}$, C$_{2-5}$, C$_{2-4}$, C$_{2-3}$, C$_{3-6}$, C$_{3-5}$, C$_{3-4}$, C$_{4-6}$, C$_{4-5}$ and C$_{5-6}$ alkyl.

"C$_{1-6}$ alkyl" refers to a radical of a straight or branched, saturated hydrocarbon group having 1 to 6 carbon atoms. In some embodiments, C$_{1-4}$ alkyl is alternative. Examples of C$_{1-6}$ alkyl include methyl (C$_1$), ethyl (C$_2$), n-propyl (C$_3$), iso-propyl (C$_3$), n-butyl (C$_4$), tert-butyl (C$_4$), sec-butyl (C$_4$), iso-butyl (C$_4$), n-pentyl (C$_5$), 3-pentyl (C$_5$), pentyl (C$_5$), neopentyl (C$_5$), 3-methyl-2-butyl (C$_5$), tert-pentyl (C$_5$) and n-hexyl (C$_6$). The term "C$_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me (—CH$_3$), Et (—CH$_2$CH$_3$), iPr (—CH(CH$_3$)$_2$), nPr (—CH$_2$CH$_2$CH$_3$), n-Bu (—CH$_2$CH$_2$CH$_2$CH$_3$) or i-Bu (—CH$_2$CH(CH$_3$)$_2$).

"C$_{2-6}$ alkenyl" refers to a radical of a straight or branched hydrocarbon group having 2 to 6 carbon atoms and at least one carbon-carbon double bond. In some embodiments, C$_{24}$ alkenyl is alternative. Examples of C$_{2-6}$ alkenyl include vinyl (C$_2$), 1-propenyl (C$_3$), 2-propenyl (C$_3$), 1-butenyl (C$_4$), 2-butenyl (C$_4$), butadienyl (C$_4$), pentenyl (C$_5$), pentadienyl (C$_5$), hexenyl (C$_6$), etc. The term "C$_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"C$_{2-6}$ alkynyl" refers to a radical of a straight or branched hydrocarbon group having 2 to 6 carbon atoms, at least one carbon-carbon triple bond and optionally one or more carbon-carbon double bonds. In some embodiments, C$_{24}$ alkynyl is alternative. Examples of C$_{2-6}$ alkynyl include, but are not limited to, ethynyl (C$_2$), 1-propynyl (C$_3$), 2-propynyl (C$_3$), 1-butynyl (C$_4$), 2-butynyl (C$_4$), pentynyl (C$_5$), hexynyl (C$_6$), etc. The term "C$_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"C$_{1-6}$ alkylene, C$_{2-6}$ alkenylene or C$_{2-6}$ alkynylene" refers to a divalent group of the "C$_{1-6}$ alkyl, C$_{2-6}$ alkenyl or C$_{2-6}$ alkynyl" as defined above.

"C$_{1-6}$ alkylene" refers to a divalent group formed by removing another hydrogen of the C$_{1-6}$ alkyl, and can be substituted or unsubstituted. In some embodiments, C$_{1-4}$ alkylene is yet alternative. The unsubstituted alkylene groups include, but are not limited to, methylene (—CH$_2$—), ethylene (—CH$_2$CH$_2$—), propylene (—CH$_2$CH$_2$CH$_2$—), butylene (—CH$_2$CH$_2$CH$_2$CH$_2$—), pentylene (—CH$_2$CH$_2$CH$_2$CH$_2$CH$_2$—), hexylene (—CH$_2$CH$_2$CH$_2$CH$_2$CH$_2$CH$_2$—), etc. Examples of substituted alkylene groups, such as those substituted with one or more alkyl (methyl) groups, include, but are not limited to, substituted methylene (—CH(CH$_3$)—, —C(CH$_3$)$_2$—), substituted ethylene (—CH(CH$_3$)CH$_2$—, —CH$_2$CH(CH$_3$)—, —C(CH$_3$)$_2$CH$_2$—, —CH$_2$C(CH$_3$)$_2$—), substituted propylene (—CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—), etc.

"C$_{2-6}$ alkenylene" refers to a C$_{2-6}$ alkenyl group wherein another hydrogen is removed to provide a divalent radical of alkenylene, and which may be substituted or unsubstituted. In some embodiments, C$_{24}$ alkenylene is yet alternative. Exemplary unsubstituted alkenylene groups include, but are not limited to, ethenylene (—CH=CH—) and propenylene (e.g., —CH=CHCH$_2$—, —CH$_2$—CH=CH—). Exemplary substituted alkenylene groups, e.g., substituted with one or more alkyl (methyl) groups, include but are not limited to, substituted ethenylene(—C(CH$_3$)=CH—, —CH=C(CH$_3$)—), substituted propenylene (e.g., —C(CH$_3$)=CHCH$_2$—, —CH=C(CH$_3$)CH$_2$—, —CH=CHCH(CH$_3$)—, —CH=CHC(CH$_3$)$_2$—, —CH(CH$_3$)—CH=CH—, —C(CH$_3$)$_2$—CH=CH—, —CH$_2$—C(CH$_3$)=CH—, —CH$_2$—CH=C(CH$_3$)—), and the like.

"C$_{2-6}$ alkynylene" refers to a C$_{2-6}$ alkynyl group wherein another hydrogen is removed to provide a divalent radical of alkynylene, and which may be substituted or unsubstituted. In some embodiments, C$_{24}$ alkynylene is yet alternative. Exemplary alkynylene groups include, but are not limited to, ethynylene (—C≡C—), substituted or unsubstituted propynylene (—C≡CCH$_2$—), and the like.

"Halo" or "halogen" refers to fluorine (F), chlorine (Cl), bromine (Br) and iodine (I).

Thus, "C$_{1-6}$ haloalkyl" refers to the above "C$_{1-6}$ alkyl", which is substituted by one or more halogen. In some embodiments, C$_{1-4}$ haloalkyl is yet alternative, and still alternatively C$_{1-2}$ haloalkyl. Exemplary haloalkyl groups include, but are not limited to, —CF$_3$, —CH$_2$F, —CHF$_2$, —CHFCH$_2$F, —CH$_2$CHF$_2$, —CF$_2$CF$_3$, —CCl$_3$, —CH$_2$Cl, —CHCl$_2$, 2,2,2-trifluoro-1,1-dimethyl-ethyl, and the like. The haloalkyl can be substituted at any available point of attachment, for example, with 1 to 5 substituents, 1 to 3 substituents or 1 substituent.

"C$_{3-10}$ cycloalkyl" refers to a radical of a non-aromatic cyclic hydrocarbon group having from 3 to 10 ring carbon atoms and zero heteroatoms. In some embodiments, C$_{3-7}$ cycloalkyl and C$_{3-6}$ cycloalkyl are yet alternative, and still alternatively C$_{5-6}$ cycloalkyl. The cycloalkyl also includes a ring system in which the cycloalkyl described herein is fused with one or more aryl or heteroaryl groups, wherein the point of attachment is on the cycloalkyl ring, and in such case, the number of carbon atoms continues to represent the number of carbon atoms in the cycloalkyl system. Exemplary cycloalkyl groups include, but are not limited to, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), cycloheptyl (C$_7$), cycloheptenyl (C$_7$), cycloheptadienyl (C$_7$), cycloheptatrienyl (C$_7$), etc. The cycloalkyl can be substituted with one or more substituents, for example, with 1 to 5 substituents, 1 to 3 substituents or 1 substituent.

"C$_{3-10}$ halocycloalkyl" refers to the above "C$_{3-10}$ cycloalkyl", which is substituted by one or more halogen.

"3- to 12-membered heterocyclyl" refers to a radical of 3- to 12-membered non-aromatic ring system having ring carbon atoms and 1 to 5 ring heteroatoms, wherein each of the heteroatoms is independently selected from nitrogen, oxygen, sulfur, boron, phosphorus and silicon. In the heterocyclyl containing one or more nitrogen atoms, the point of attachment can be a carbon or nitrogen atom as long as the valence permits. In some embodiments, 4- to 12-membered heterocyclyl is alternative, which is a radical of 4- to 12-membered non-aromatic ring system having ring carbon atoms and 1 to 5 ring heteroatoms. In some embodiments, 3- to 10-membered heterocyclyl is alternative, which is a radical of 3- to 10-membered non-aromatic ring system having ring carbon atoms and 1 to 5 ring heteroatoms. In some embodiments, 3- to 7-membered heterocyclyl is alternative, which is a radical of 3- to 7-membered non-aromatic ring system having ring carbon atoms and 1 to 4 ring heteroatoms. 3 to 6-membered heterocyclyl is alternative, which is a radical of 3- to 6-membered non-aromatic ring system having ring carbon atoms and 1 to 3 ring heteroatoms. 4- to 8-membered heterocyclyl is alternative, which is a radical of 4- to 8-membered non-aromatic ring system having ring carbon atoms and 1 to 3 ring heteroatoms. 5- to 6-membered heterocyclyl is more alternative, which is a radical of 5- to 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the cycloalkyl ring, or the heterocyclyl described above is fused with one or more aryl or heteroaryl groups, wherein the point of attachment is on the heterocyclyl ring; and in such cases, the number of ring members continues to represent the number of ring members in the heterocyclyl ring system. Exemplary 3-membered heterocyclyl groups containing one heteroatom include, but are not limited to, aziridinyl, oxiranyl and thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothienyl, pyrrolidinyl, dihydropyrrolyl and pyrrolyl-2,5-dione. Exemplary 5-membered heterocyclyl groups containing two heteroatoms include, but are not limited to, dioxolanyl, oxasulfuranyl, disulfuranyl, and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidyl, tetrahydropyranyl, dihydropyridyl and thianyl. Exemplary 6-membered heterocyclyl groups containing two heteroatoms include, but are not limited to, piperazinyl, morpholinyl, dithianyl and dioxanyl. Exemplary 6-membered heterocyclyl groups containing three heteroatoms include, but are not limited to, triazinanyl. Exemplary 7-membered heterocyclyl groups containing one heteroatom include, but are not limited to, azepanyl, oxepanyl and thiepanyl. Exemplary 5-membered heterocyclyl groups fused with a $C_6$ aryl (also referred as 5,6-bicyclic heterocyclyl herein) include, but are not limited to, indolinyl, isoindolinyl, dihydrobenzofuranyl, dihydrobenzothiophenyl, benzoxazolinonyl, etc. Exemplary 6-membered heterocyclyl groups fused with a $C_6$ aryl (also referred as 6,6-bicyclic heterocyclyl herein) include, but are not limited to, tetrahydroquinolinyl, tetrahydroisoquinolinyl, etc. The heterocyclyl can be substituted with one or more substituents, for example, with 1 to 5 substituents, 1 to 3 substituents or 1 substituent.

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared π electrons in a cyclic array). In some embodiments, the aryl group has six ring carbon atoms ("$C_6$ aryl"; for example, phenyl). In some embodiments, the aryl group has ten ring carbon atoms ("$C_{10}$ aryl"; for example, naphthyl, e.g., 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system. The aryl can be substituted with one or more substituents, for example, with 1 to 5 substituents, 1 to 3 substituents or 1 substituent.

"5- to 10-membered heteroaryl" refers to a radical of 5- to 10-membered monocyclic or bicyclic 4n+2 aromatic ring system (e.g., having 6 or 10 shared π electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. Heteroaryl bicyclic systems may include one or more heteroatoms in one or two rings. Heteroaryl also includes ring systems wherein the heteroaryl ring described above is fused with one or more cycloalkyl or heterocyclyl groups, and the point of attachment is on the heteroaryl ring. In such case, the number the carbon atoms continues to represent the number of carbon atoms in the heteroaryl ring system. In some embodiments, 5- to 6-membered heteroaryl groups are yet alternative, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl (such as, 1,2,4-oxadiazolyl), and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6,6-bicyclic heteroaryl groups include, but are not limited to, naphthyridinyl, pteridinyl, quinolyl, isoquinolyl, cinnolinyl, quinoxalinyl, phthalazinyl and quinazolinyl. The heteroaryl can be substituted with one or more substituents, for example, with 1 to 5 substituents, 1 to 3 substituents or 1 substituent.

Alternatively, specific examples of heteroaryl groups include: pyrrolyl, imidazolyl, pyrazolyl, 2-pyridyl, 3-pyridyl, 4-pyridyl, pyrimidinyl, pyrazinyl, pyridazinyl, triazolyl (4H-1,2,4-triazolyl, 1H-1,2,3-triazolyl, 2H-1,2,3-triazolyl), pyranyl, 2-furanyl, 3-furanyl, etc., 2-thienyl, 3-thienyl, oxazolyl, isoxazolyl, oxadiazolyl (1,2,4-oxazolyl, 1,3,4-oxazolyl, 1,2,5-oxazolyl), thiazolyl, thiadiazolyl (1,2,4-thiadiazolyl, 1,3,4-thiadiazolyl, 1,2,5-thiadiazolyl), triazinyl or tetrazinyl.

The term "natural amino acid" is the basic structural unit of protein, which is the basis for later modification of protein by organisms. There are 20 kinds of natural amino acids in total. In addition, on the basis of these basic amino acids, organisms can also synthesize some kinds of derived amino acids such as hydroxyproline, hydroxylysine, and the like. In fireflies, even D-form amino acid can be synthesized. These biosynthetic amino acids are collectively referred to as "natural amino acids". Natural amino acids are generally L-form. The 20 most common natural amino acids are shown in the Table below:

| Abbreviation | Name | Branch | Molecular Weight | Isoelectric Point | R group |
|---|---|---|---|---|---|
| Gly | G | Glycine | Hydrophilic | 75.07 | 5.97 | —H |
| Ala | A | Alanine | Hydrophobic | 89.09 | 6.02 | —$CH_3$ |
| Val | V | Valine | Hydrophobic | 117.15 | 6.48 | —$CH(CH_3)_2$ |
| Leu | L | Leucine | Hydrophobic | 131.17 | 5.98 | —$CH_2$—$CH(CH_3)_2$ |
| Ile | I | Isoleucine | Hydrophobic | 131.17 | 6.05 | —$CH(CH_3)$—$CH_2$—$CH_3$ |
| Phe | F | Phenylalanine | Hydrophobic | 165.19 | 5.49 | —$CH_2$—$C_6H_5$ |
| Trp | W | Tryptophan | Hydrophobic | 204.23 | 5.89 | —$C_8NH_6$ |
| Tyr | Y | Tyrosine | Hydrophilic | 181.19 | 5.64 | —$CH_2$—$C_6H_4$—OH |
| Asp | D | Aspartic acid | Acidic | 133.10 | 2.85 | —$CH_2$—COOH |
| Asn | N | Asparagine | Hydrophilic | 132.12 | 5.41 | —$CH_2$—$CONH_2$ |
| Glu | E | Glutamic acid | Acidic | 147.13 | 3.15 | —$(CH_2)_2$—COOH |
| Lys | K | Lysine | Alkaline | 146.19 | 9.60 | —$(CH_2)_4$—$NH_2$ |
| Gln | Q | Glutamine | Hydrophilic | 146.15 | 5.65 | —$(CH_2)_2$—$CONH_2$ |
| Met | M | Methionine | Hydrophobic | 149.21 | 5.74 | —$(CH_2)_2$—S—$CH_3$ |
| Ser | S | Serine | Hydrophilic | 105.09 | 5.68 | —$CH_2$—OH |
| Thr | T | Threonine | Hydrophilic | 119.12 | 5.60 | —$CH(CH_3)$—OH |
| Cys | C | Cysteine | Hydrophilic | 121.16 | 5.05 | —$CH_2$—SH |
| Pro | P | Proline | Hydrophobic | 115.13 | 6.30 | —$C_3H_6$ |
| His | H | Histidine | Alkaline | 155.16 | 7.60 | —$CH_2$—$C_3H_3N_2$ |
| Arg | R | Arginine | Alkaline | 174.20 | 10.76 | —$(CH_2)_3$—$NHC(NH)NH_2$ |

As used in this specification and in the claims, "and/or" should be understood to mean "either or both" of the associated elements, i.e., the elements exist jointly in some cases and separately in other cases. Multiple elements listed with "and/or" should be construed in the same fashion, i.e., "one or more" of the associated elements. In addition to the elements specifically identified by the "and/or" clause, other elements may optionally exist, whether related or unrelated to those elements specifically identified. Thus, as a non-limiting example, a reference to "A and/or B", when used in conjunction with open-ended language such as "comprising", can refer, in one embodiment, to A only (optionally including elements other than B); in another embodiment, to B only (optionally including elements other than A); in yet another embodiment, to both A and B (optionally including other elements); etc.

Abbreviations used herein have their usual meanings in the fields of chemistry, biology and formulation.

The compounds of formula (I) of the present disclosure contain one or more asymmetric centers and thus may exist in various stereoisomeric forms, e.g., enantiomeric and/or diastereomeric forms. For example, the compounds of the present disclosure may be individual enantiomers, diastereomers or geometric isomers (such as cis and trans isomers), or may be in the form of mixtures of stereoisomers comprising racemic mixtures and mixtures enriched in one or more stereoisomers. Isomers can be separated from mixtures by methods known to those skilled in the art, including chiral high pressure liquid chromatography (HPLC) and formation and crystallization of chiral salts; or alternative isomers may be prepared by asymmetric synthesis.

The present disclosure also comprises compounds that are labeled with isotopes, which are equivalent to the prodrug, but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$ $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^3H$ and $^{14}C$), can be used for the measurement of the distribution of drug and/or substrate in tissue. Tritium, which is $^3H$ and carbon-14, which is $^{14}C$ isotope, are yet alternative, because they are easy to be prepared and detected. Furthermore, replaced by heavier isotopes, such as deuterium, which is $^2H$, may provide therapeutic benefits due to the higher metabolic stability, such as prolonging the half-life in vivo or decreasing the dosage requirements, and thus may be alternative in some cases. Isotope-labeled compounds of formula (I) of the present disclosure can be prepared generally by using readily available isotope-labeled reagents to replace non-isotope-labeled reagents in the following schemes and/or the procedures disclosed in the examples and preparation examples.

By "pharmaceutically available" or "pharmaceutically acceptable", it is meant a material which is not biologically or otherwise undesirable, i.e., the material may be administered to an individual without causing any undesirable biological effects or interacting in a deleterious manner with any other component of a composition comprising the material.

The term "pharmaceutically acceptable salt" refers to a salt that does not irritate an organism significantly and retains the biological activity and properties of a compound.

The term "pharmaceutically acceptable carrier" refers to an inactive ingredient that does not irritate an organism significantly and does not abrogate the biological activity and properties of an administered compound. As used herein, "carrier" and "excipient" have the same meaning.

The term "therapeutically effective amount" refers to an amount of an agent sufficient to provide a desired biological result. The result may be reduction and/or alleviation of a sign, symptom, or cause of a disease, or any other desired change of a biological system. For example, a "therapeutically effective amount" for therapeutic use refers to a necessary amount of a composition comprising a compound disclosed herein as an active ingredient for providing a clinically significant decrease in a disease. In any individual case, an appropriate "therapeutically effective amount" may be determined by one of ordinary skill in the art using routine experimentation. Thus, the expression "therapeutically effective amount" generally refers to an amount of an active substance at which it has a therapeutic effect.

As used herein, the term "treat" is synonymous with the terms "prevent" and "alleviate", and is intended to mean delaying disease progression, preventing disease progression and/or reducing the severity of symptoms that will develop or are expected to develop. Thus, these terms include ameliorating existing disease symptoms, preventing additional symptoms, ameliorating or preventing underlying metabolic causes of symptoms, inhibiting disorder or disease, e.g., preventing the development of disorder or disease, relieving disorder or disease, causing a regression of disorder or disease, relieving a condition caused by disease or disorder, or stopping symptoms of disease or disorder.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present disclosure, the mammal is a human. The term "subject" includes a confirmed patient, but the "subject" does not need to have any special identity to a hospital, clinic, or research facility (e.g., as a confirmed patient, study participant, etc.).

It is to be understood that the terminology employed herein is for the purpose of describing particular embodiments, but not intended to be limiting. Further, alternative methods, devices and materials are described below, although any methods, devices and materials similar or equivalent to those described herein can be used in the practice or testing of the present invention.

DETAILED EMBODIMENTS

Figure 1:
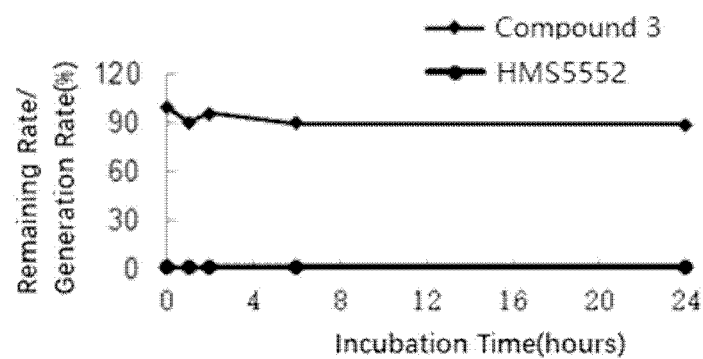
FIG. 1 is a graph showing the comparison of remaining rate/generation rate-incubation time of compound 3 and HMS5552 in artificial simulated gastric fluid.

In one embodiment, the present disclosure relates to a compound of formula (I), or an isotopically labeled product, an enantiomer, a diastereomer or a pharmaceutically acceptable salt thereof:

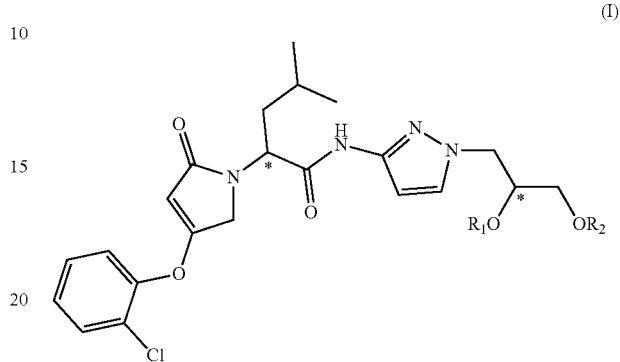

wherein
* indicates a chiral center,
$R_1$ is selected from H, —C(O)$R_6$, —C(O)O$R_6$, —C(O)N$R_7R_8$, —S(O)$_m$$R_6$, —S(O)$_m$O$R_6$, or —S(O)$_m$N$R_7R_8$;
$R_2$ is selected from —C(O)$R_3$, —C(O)O$R_3$, —C(O)N$R_4R_5$, —S(O)$_m$$R_3$, —S(O)$_m$O$R_3$, or —S(O)$_m$N$R_4R_5$;
or $R_1$ and $R_2$ are connected to form —CHR$_d$—, —SiR$_d$R$_e$—, —C(O)—, —S(O)$_{1-2}$-, —P(O)OR$_d$—, or —CR$_d$R$_e$—CR$_d$R$_e$—;
$R_3$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl, which is optionally substituted with 1, 2, 3, 4 or 5 R groups;
$R_4$ and $R_5$ are independently selected from H, $C_{1-6}$ alkyl, $C_{2-6}$ alkenyl, $C_{2-6}$ alkynyl, or $C_{1-6}$ haloalkyl; alternatively, $R_4$ and $R_5$ are taken together with the N atom to form 3- to 7-membered heterocyclyl;
$R_6$ is independently selected from H, $C_{1-6}$ alkyl, $C_{2-6}$ alkenyl, $C_{2-6}$ alkynyl, or $C_{1-6}$ haloalkyl;
$R_7$ and $R_8$ are independently selected from H, $C_{1-6}$ alkyl, $C_{2-6}$ alkenyl, $C_{2-6}$ alkynyl, or $C_{1-6}$ haloalkyl; alternatively, $R_7$ and $R_8$ are taken together with the N atom to form 3- to 7-membered heterocyclyl;
R is independently selected from H, -L-halogen, -L-CN, -L-NO$_2$, -L-OR$_a$, -L-SR$_a$, -L-NR$_b$R$_c$, -L-C(O)OR$_a$, -L-C(O)NR$_b$R$_c$, -L-S(O)$_m$OR$_a$, -L-S(O)$_m$NR$_b$R$_c$, $C_{1-6}$ alkyl, $C_{1-6}$ haloalkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, 5- to 10-membered heteroaryl, or a side chain of a natural amino acid;
wherein m is 1 or 2;
$R_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;
$R_b$ and $R_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; alternatively, $R_b$ and $R_c$ are taken together with the N atom to form 3- to 7-membered heterocyclyl;

$R_d$ and $R_e$ are independently selected from H, $C_{1-6}$ alkyl, $C_{2-6}$ alkenyl, $C_{2-6}$ alkynyl, or $C_{1-6}$ haloalkyl; alternatively, $R_d$ and $R_e$ are taken together with the C atom to form =O, =S, $C_3$-7 cycloalkyl, or 3- to 7-membered heterocyclyl;

L is selected from a chemical bond, —$C_{1-6}$ alkylene-, —$C_{2-6}$ alkenylene-, or —$C_{2-6}$ alkynylene-.

In another embodiment, the present disclosure relates to the above-mentioned compound or isotopically labeled product, enantiomer, diastereomer or pharmaceutically acceptable salt thereof, wherein the compound is of the following structures:

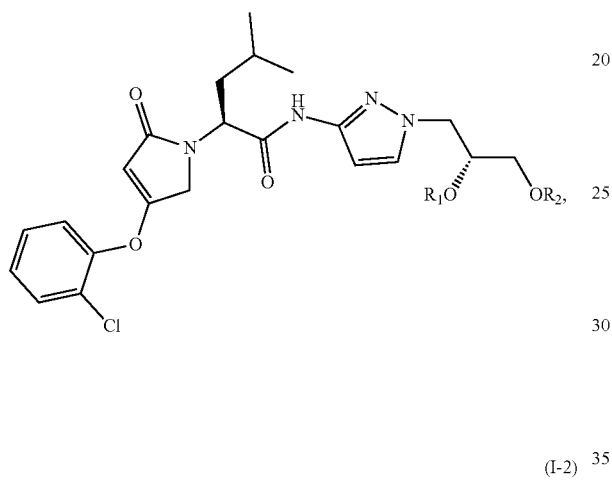

(I-1)

(I-2)

(I-3)

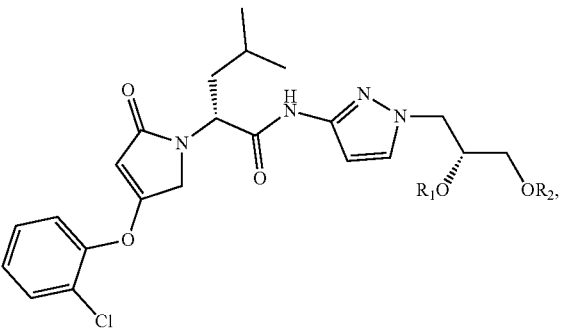

(I-4)

wherein $R_1$ is selected from H, —C(O)$R_6$, —C(O)O$R_6$, or —C(O)N$R_7R_8$;

$R_2$ is selected from —C(O)$R_3$, —C(O)O$R_3$, or —C(O)N$R_4R_5$;

or $R_1$ and $R_2$ are connected to form —Si$R_dR_e$—, —C(O)—, —S(O)$_{1-2}$-, —P(O)O$R_d$—, or —C$R_dR_e$—C$R_dR_e$—;

$R_3$ is independently selected from H, $C_{1-6}$ alkyl, $C_{2-6}$ alkenyl, $C_{2-6}$ alkynyl, or $C_{1-6}$ haloalkyl;

$R_4$ and $R_5$ are independently selected from H, $C_{1-6}$ alkyl, $C_{2-6}$ alkenyl, $C_{2-6}$ alkynyl, or $C_{1-6}$ haloalkyl; alternatively, $R_4$ and $R_5$ are taken together with the N atom to form 3- to 7-membered heterocyclyl;

$R_6$ is independently selected from H, $C_{1-6}$ alkyl, $C_{2-6}$ alkenyl, $C_{2-6}$ alkynyl, or $C_{1-6}$ haloalkyl;

$R_7$ and $R_8$ are independently selected from H, $C_{1-6}$ alkyl, $C_{2-6}$ alkenyl, $C_{2-6}$ alkynyl, or $C_{1-6}$ haloalkyl; alternatively, $R_7$ and $R_8$ are taken together with the N atom to form 3- to 7-membered heterocyclyl;

$R_d$ and $R_e$ are independently selected from H, $C_{1-6}$ alkyl, $C_{2-6}$ alkenyl, $C_{2-6}$ alkynyl, or $C_{1-6}$ haloalkyl; alternatively, $R_d$ and $R_e$ are taken together with the C atom to form =O, =S, $C_3$-7 cycloalkyl, or 3- to 7-membered heterocyclyl.

In another embodiment, the present disclosure relates to the above-mentioned compound or isotopically labeled product, enantiomer, diastereomer or pharmaceutically acceptable salt thereof, wherein $R_1$ is selected from H, —COMe, or —COOEt, $R_2$ is selected from —COMe, —COOEt, or —CONHMe;

or $R_1$ and $R_2$ are connected to form —CHMe-, —SiMe$_2$-, —C(O)—, —S(O)$_{1-2}$-, or —P(O)OEt-.

In another embodiment, the present disclosure relates to the above-mentioned compound or isotopically labeled product, enantiomer, diastereomer or pharmaceutically acceptable salt thereof, wherein the compound is of the following structures:

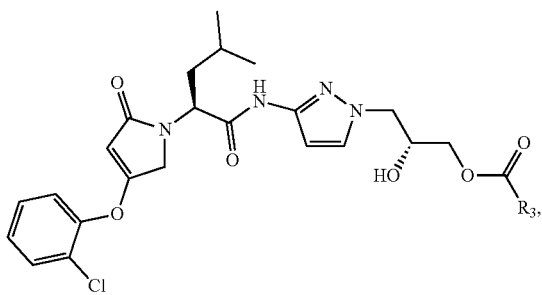

(II-1)

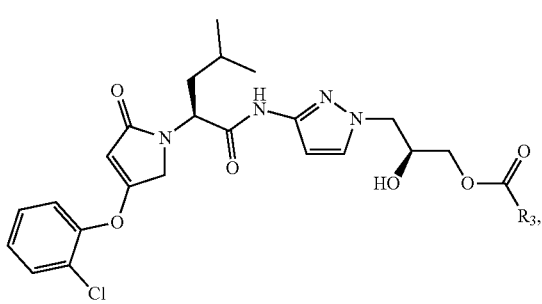

(II-2)

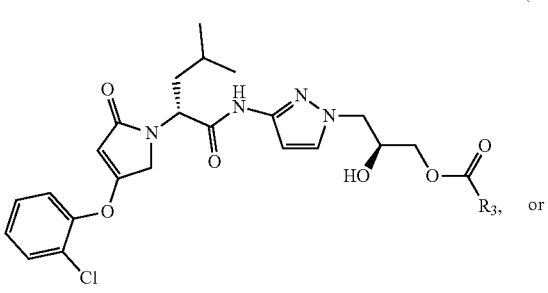

(II-3) or

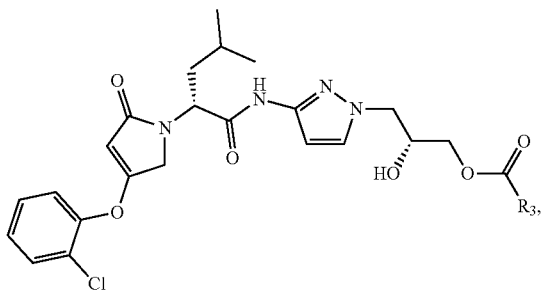

(II-4)

wherein
R$_3$ is selected from C$_{3-7}$ cycloalkyl, 3- to 7-membered heterocyclyl, C$_{6-10}$ aryl, or 5- to 10-membered heteroaryl, which is optionally substituted with 1, 2, 3, 4 or 5 R groups;
R is independently selected from H, -L-halogen, -L-CN, -L-NO$_2$, -L-OR$_a$, -L-SR$_a$, -L-NR$_b$R$_c$, -L-C(O)OR$_a$, -L-C(O)NR$_b$R$_c$, -L-S(O)$_m$OR$_a$, -L-S(O)$_m$NR$_b$R$_c$, C$_{1-6}$ alkyl, C$_{1-6}$ haloalkyl, C$_{2-6}$ alkenyl, or C$_{2-6}$ alkynyl;
wherein m is 1 or 2;
R$_a$ is independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, or 5- to 10-membered heteroaryl;
R$_b$ and R$_c$ are independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, or 5- to 10-membered heteroaryl; alternatively, R$_b$ and R$_c$ are taken together with the N atom to form 3- to 7-membered heterocyclyl;
L is selected from a chemical bond, —C$_{1-6}$ alkylene-, —C$_{2-6}$ alkenylene-, or —C$_{2-6}$ alkynylene-.

In another embodiment, the present disclosure relates to the above-mentioned compound or isotopically labeled product, enantiomer, diastereomer or pharmaceutically acceptable salt thereof, wherein
R$_3$ is selected from C$_{6-10}$ aryl or 5- to 6-membered heteroaryl, which is optionally substituted with 1, 2, 3, 4 or 5 R groups;
R is independently selected from H, halogen, —CN, —NO$_2$, —OH, —SH, —NH$_2$, —C(O)OH, —C(O)NH$_2$, —S(O)$_m$OH, —S(O)$_m$NH$_2$, C$_{1-6}$ alkyl, C$_{1-6}$ haloalkyl, C$_{2-6}$ alkenyl, or C$_{2-6}$ alkynyl;
wherein m is 1 or 2.

In another embodiment, the present disclosure relates to the above-mentioned compound or isotopically labeled product, enantiomer, diastereomer or pharmaceutically acceptable salt thereof, wherein
R$_3$ is selected from phenyl, naphthyl, pyrrolyl, furyl, thienyl, imidazolyl, pyrazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, triazinyl or tetrazinyl, which is optionally substituted with 1, 2, 3, 4 or 5 R groups;
R is independently selected from H, halogen, —CN, —NO$_2$, —OH, —SH, —NH$_2$, —C(O)OH, —C(O)NH$_2$, —S(O)$_m$OH, or —S(O)$_m$NH$_2$;
wherein m is 1 or 2.

In another embodiment, the present disclosure relates to the above-mentioned compound or isotopically labeled product, enantiomer, diastereomer or pharmaceutically acceptable salt thereof, wherein
R$_3$ is selected from phenyl, pyridyl, pyridazinyl, pyrimidinyl, pyrazinyl, triazinyl, or tetrazinyl, which is optionally substituted with 1, 2 or 3 R groups;
R is independently selected from H, halogen, —CN, —NO$_2$, —OH, —SH, or —NH$_2$.

In another embodiment, the present disclosure relates to the above-mentioned compound or isotopically labeled product, enantiomer, diastereomer or pharmaceutically acceptable salt thereof, wherein the compound is of the following structures:

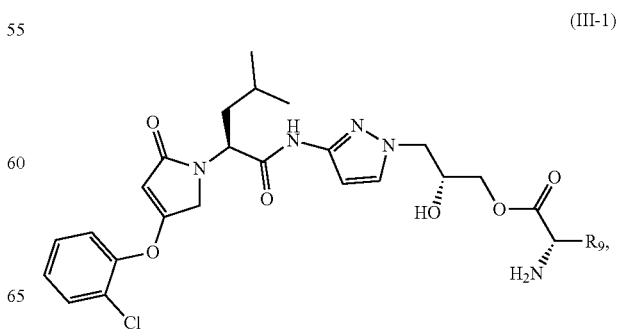

(III-1)

-continued (III-2)

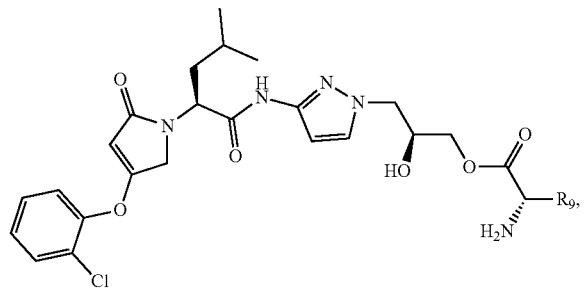

(III-3)

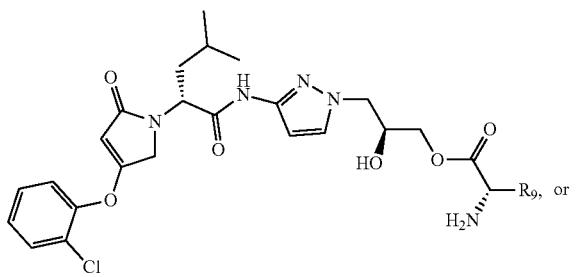

(III-4)

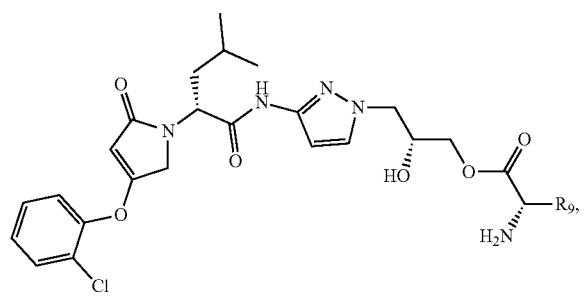

wherein
$R_9$ is selected from H, -L-halogen, -L-CN, -L-NO$_2$, -L-OR$_a$, -L-SR$_a$, -L-NR$_b$R$_c$, -L-C(O)OR$_a$, -L-C(O)NR$_b$R$_c$, -L-S(O)$_m$OR$_a$, -L-S(O)$_m$NR$_b$R$_c$, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, 5- to 10-membered heteroaryl, or a side chain of a natural amino acid;

wherein m is 1 or 2;

$R_a$ is independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, or 5- to 10-membered heteroaryl;

$R_b$ and $R_c$ are independently selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, or 5- to 10-membered heteroaryl; alternatively, $R_b$ and $R_c$ are taken together with the N atom to form 3- to 7-membered heterocyclyl;

L is selected from a chemical bond, —C$_{1-6}$ alkylene-, —C$_{2-6}$ alkenylene-, or —C$_{2-6}$ alkynylene-.

In another embodiment, the present disclosure relates to the above-mentioned compound or isotopically labeled product, enantiomer, diastereomer or pharmaceutically acceptable salt thereof, wherein $R_9$ is selected from H, C$_{1-6}$ alkyl, C$_{2-6}$ alkenyl, C$_{2-6}$ alkynyl, C$_{1-6}$ haloalkyl, C$_{3-7}$ cycloalkyl, 3- to 7-membered heterocyclyl, C$_{6-10}$ aryl, 5- to 10-membered heteroaryl, or a side chain of a natural amino acid.

In another embodiment, the present disclosure relates to the above-mentioned compound or isotopically labeled product, enantiomer, diastereomer or pharmaceutically acceptable salt thereof, wherein $R_9$ is selected from a side chain of the following natural amino acids: glycine, alanine, valine, leucine, isoleucine, phenylalanine, tryptophan, tyrosine, aspartic acid, asparagine, glutamic acid, lysine, glutamine, methionine, serine, threonine, cysteine, proline, histidine, and arginine.

In another embodiment, the present disclosure relates to the above-mentioned compound or isotopically labeled product, enantiomer, diastereomer or pharmaceutically acceptable salt thereof, wherein $R_9$ is alanine side chain (Me) or valine side chain (iPr).

Any technical solution in any of the above specific embodiments or any combination thereof may be combined with any technical solution in other specific embodiments or any combination thereof. The present disclosure is intended to include all the combinations of these technical solutions, which are not listed one by one due to space limitations.

In another embodiment, the present disclosure relates to the above-mentioned compound or isotopically labeled product, enantiomer, diastereomer or pharmaceutically acceptable salt thereof, wherein the representative compound is selected from

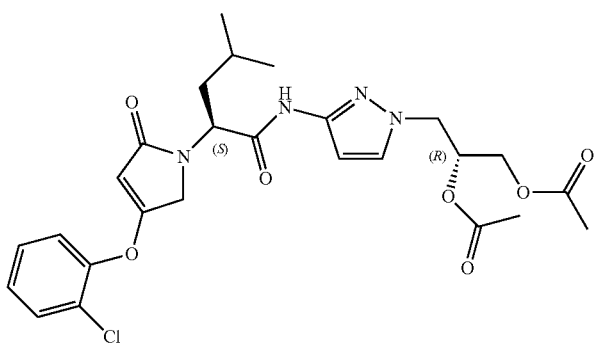

-continued
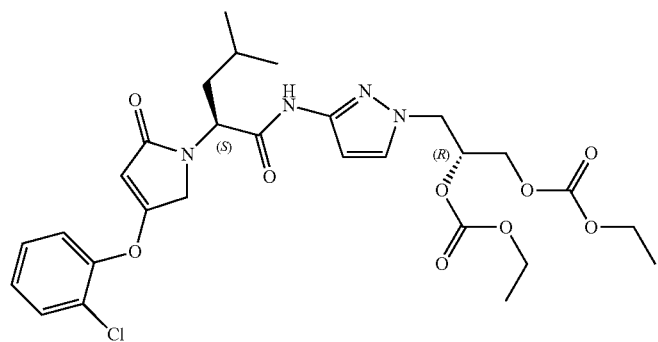
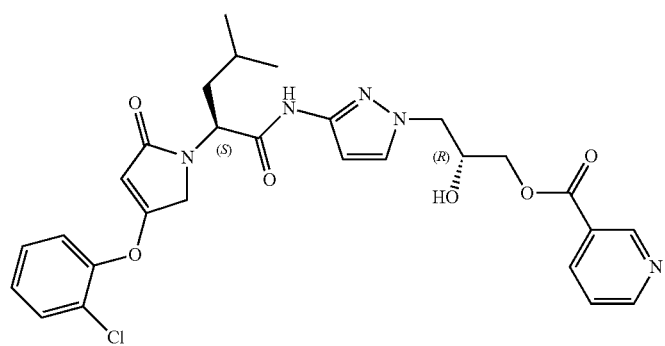
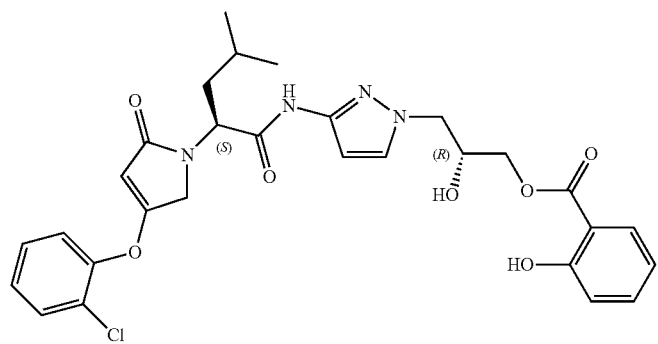
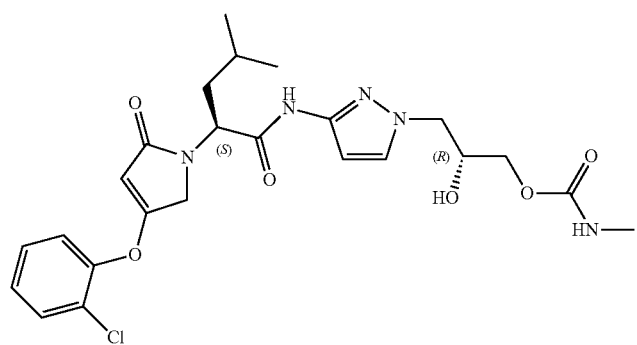
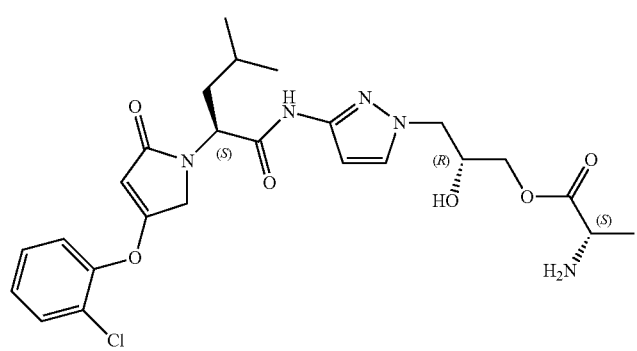

-continued

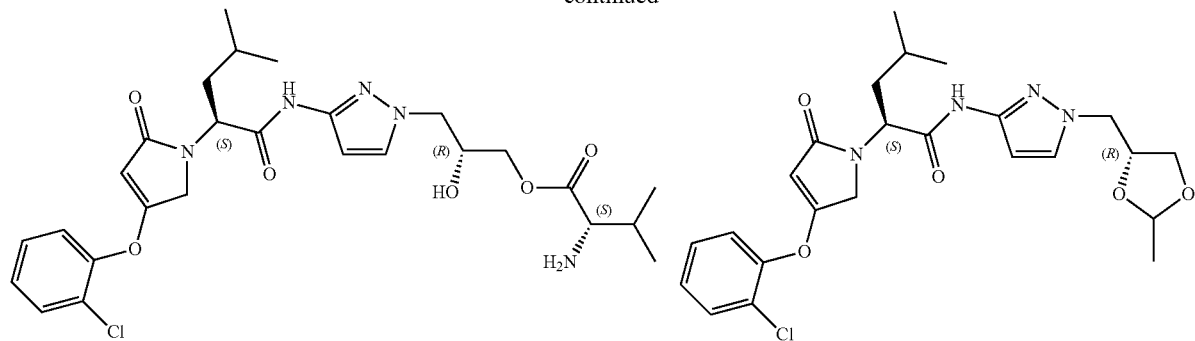

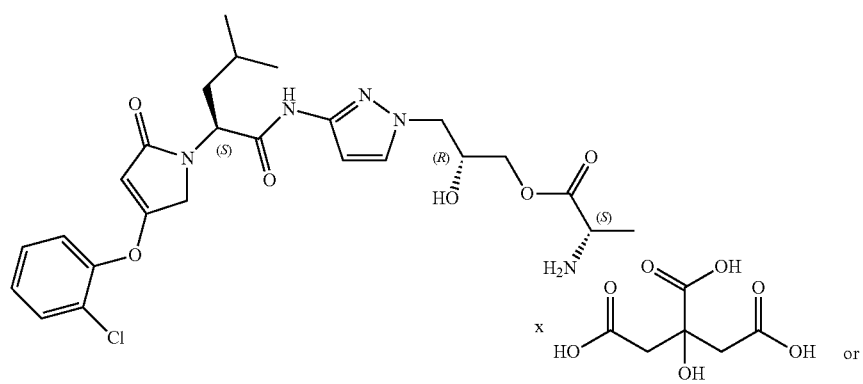

or

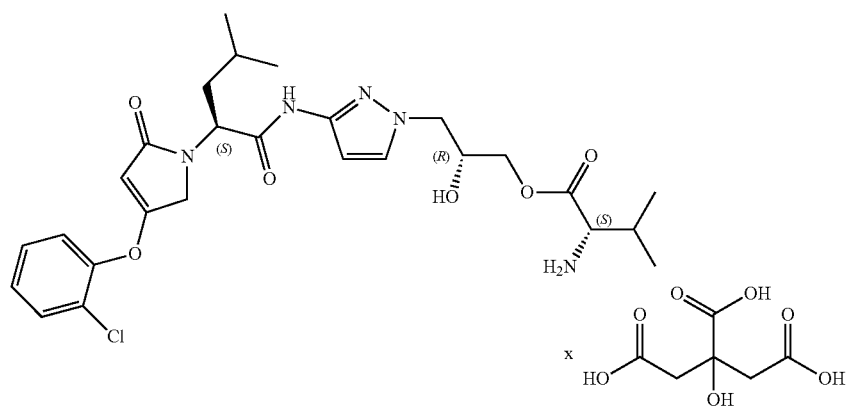

or a pharmaceutically acceptable salt thereof.

Drug Combination and/or Pharmaceutical Composition

The compounds of the present disclosure may be used alone or in combination with other therapeutic agents to treat a variety of conditions or diseases. The compounds of the present disclosure and other therapeutic agents may be administered simultaneously (in the same dosage form or in separate dosage forms) or sequentially.

In one embodiment, the other therapeutic agent in combination with the drug of the present disclosure is a glucose-lowering agent.

In another embodiment, provided herein is a pharmaceutical composition comprising a compound of the present disclosure, or an isotopically labeled product, an enantiomer, a diastereoisomer, or a pharmaceutically acceptable salt thereof; and optionally one or more pharmaceutically acceptable excipients.

Use for Treatment and/or Prevention of Disease

A further embodiment of the present disclosure relates to use of a compound of formula (I), or an isotopically labeled product, an enantiomer, a diastereoisomer, or a pharmaceutically acceptable salt thereof; or a pharmaceutical composition thereof in the manufacture of a medicament. In particular, a specific embodiment of the present disclosure relates to the use of a compound of formula (I) of the present disclosure, or an isotopically labeled product, an enantiomer, a diastereoisomer, or a pharmaceutically acceptable salt thereof, or a pharmaceutical composition thereof in the manufacture of a medicament for the treatment and/or prevention of the following diseases and medical conditions, in particular one or more diseases selected from type I diabetes mellitus, type II diabetes mellitus, impaired glucose tolerance, impaired fasting blood glucose, hyperglycemia, postprandial hyperglycemia, overweight, obesity, hypertension, insulin resistance, and metabolic syndrome.

A further embodiment of the present disclosure relates to use of a compound of formula (I) of the present disclosure, or an isotopically labeled product, an enantiomer, a diastereoisomer, or a pharmaceutically acceptable salt thereof, or a pharmaceutical composition thereof in the manufacture of a medicament for curing diabetes, inducing remission or regression of diabetes.

Method for Treatment and/or Prevention of Disease

A further embodiment of the present disclosure relates to a method of treating and/or preventing one or more diseases selected from type I diabetes mellitus, type II diabetes mellitus, impaired glucose tolerance, impaired fasting blood glucose, hyperglycemia, postprandial hyperglycemia, overweight, obesity, hypertension, insulin resistance, and metabolic syndrome, comprising administering to a subject a therapeutically effective amount of a compound of formula (I), or an isotopically labeled product, an enantiomer, a diastereoisomer, or a pharmaceutically acceptable salt thereof; or, administering to the subject a therapeutically effective amount of a drug combination or a pharmaceutical composition.

The method of the present disclosure for the treatment and/or prevention of diabetes mellitus and related diseases comprises:
- preventing, slowing the progression of, delaying or treating a metabolic disorder selected from the group consisting of type I diabetes mellitus, type II diabetes mellitus, impaired glucose tolerance, impaired fasting blood glucose, hyperglycemia, postprandial hyperglycemia, hypertension, overweight, obesity, insulin resistance, and metabolic syndrome; or
- curing diabetes, inducing remission or regression of diabetes; or
- improving glycemic control and/or for reducing of fasting plasma glucose, of postprandial plasma glucose and/or of glycosylated hemoglobin HbA1c; or
- preventing, slowing, delaying or reversing progression from impaired glucose tolerance, insulin resistance and/or from metabolic syndrome to type II diabetes mellitus; or
- preventing, slowing the progression of, delaying or treating of a condition or disorder selected from the group consisting of complications of diabetes mellitus such as cataracts and micro- and macrovascular diseases, such as nephropathy, retinopathy, neuropathy, learning and memory dysfunction, neurodegenerative or cognitive disorders, cardio- or cerebrovascular diseases, tissue ischaemia, diabetic foot or ulcer, arteriosclerosis, hypertension, endothelial dysfunction, myocardial infarction, acutecoronary syndrome, unstable angina pectoris, stable angina pectoris, stroke, peripheral arterial occlusive disease, cardiomyopathy, heart failure, heart rhythm disorders and vascular restenosis; or
- reducing body weight and/or body fat or preventing an increase in body weight and/or body fat or facilitating a reduction in body weight and/or body fat; or
- preventing, slowing, delaying or treating the degeneration of pancreatic beta cells and/or the decline of the functionality of pancreatic beta cells and/or for improving and/or restoring or protecting the functionality of pancreatic beta cells and/or restoring the functionality of pancreatic insulin secretion; or
- preventing, slowing, delaying or treating diseases or conditions attributed to an abnormal accumulation of liver or ectopic fat; or
- maintaining and/or improving the insulin sensitivity and/or for treating or preventing hyperinsulinemia and/or insulin resistance; or
- preventing, slowing progression of, delaying, or treating new onset diabetes after transplantation (NODAT) and/or post-transplant metabolic syndrome (PTMS); or
- preventing, delaying, or reducing NODAT and/or PTMS associated complications including micro- and macrovascular diseases and events, graft rejection, infection, and death; or
- treating hyperuricemia and hyperuricemia associated conditions.

In an alternative embodiment of the present disclosure, the disease comprises type I diabetes mellitus, type II diabetes mellitus, impaired glucose tolerance, impaired fasting blood glucose, hyperglycemia, postprandial hyperglycemia, overweight, obesity, hypertension, insulin resistance, and metabolic syndrome.

According to another embodiment, the present disclosure also provides a method of treating type II diabetes mellitus by oral administration of a therapeutically effective amount of a compound of formula (I) or a pharmaceutical composition of the present disclosure to a subject in need of the treatment. In one embodiment, the subject in need of the treatment is a human. In another embodiment, the pharmaceutical composition is in the form of a tablet.

According to another embodiment, the present disclosure also provides a method of administering to a subject one or more other combination drug treatments simultaneously or sequentially with the treatment with a therapeutically effective amount of a compound of formula (I), or an isotopically labeled product, an enantiomer, a diastereoisomer, or a pharmaceutically acceptable salt thereof, or a therapeutically effective amount of a pharmaceutical composition.

The compound of formula (I) and the pharmaceutical composition of the present disclosure can be administered once daily (QD), twice daily (BID) or three times daily (TID).

EXAMPLES

The materials or reagents used herein are commercially available or prepared by synthetic methods commonly known in the art.

The following examples further describe and illustrate embodiments that are within the scope of the present disclosure. However, the present disclosure is not limited to the examples, and any modifications and replacements made on the technical basis of the present disclosure fall within the protective scope of the present disclosure.

In the following examples, the meanings of the abbreviations shown in Table 1 may be used.

TABLE 1

Meanings of abbreviations

| Abbreviation | Meaning |
| --- | --- |
| DMF | N,N-dimethylformamide |
| HATU | 2-(7-Azabenzotriazolyl)-N,N,N',N'-tetramethyluronium hexafluorophosphate |
| HMS5552 | (S)-2-(4-(2-Chlorophenoxy)-2-oxo-2,5-dihydro-1H-pyrrol-1-yl)-N-(1-((R)-2,3-dihydroxypropyl)-1H-pyrazol-3-yl)-4-methylpentanamide |
| TBAF | Tetrabutylammonium fluoride |
| TBSCl | Tert-butyldimethylchlorosilane |
| THF | Tetrahydrofuran |
| MTBE | Methyl tert-butyl ether |

TABLE 1-continued

Meanings of abbreviations

| Abbreviation | Meaning |
|---|---|
| DMA | Dimethylacetamide |
| PEG400 | Polyethylene glycol 400 |
| Tween 80 | Tween 80 |
| PMSF | Phenylmethylsulfonyl fluoride |

Synthetic scheme

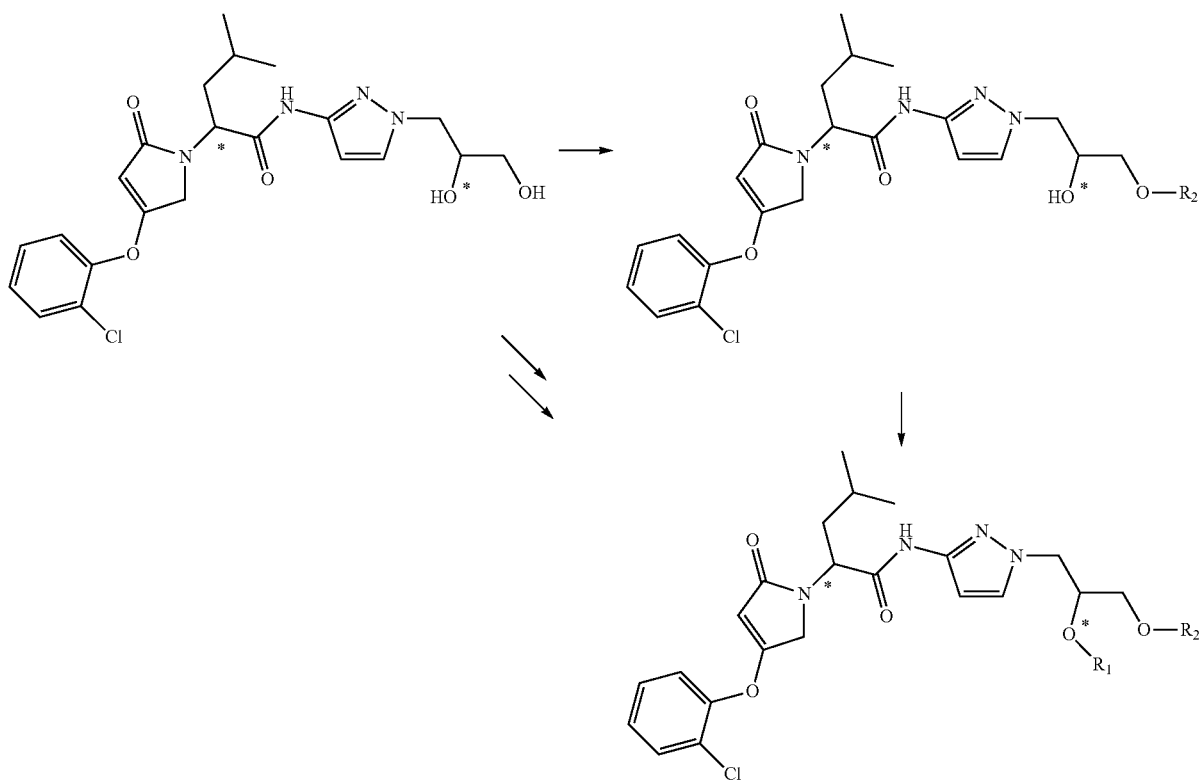

The compound HMS5552 is reacted with reagents such as acid anhydride, acid chloride, chloroformate, chloroformamide, sulfonyl chloride, acid, amino acid, or sulfonic acid in the presence of a base, and/or optionally a condensing agent, so that the primary hydroxyl group of HMS5552 is esterified by conventional esterification reaction; optionally, the secondary hydroxyl group of HMS5552 may be esterified by further reacting with the same or different reagents such as acid anhydride, acyl chloride, chloroformate, chloroformamide, sulfonyl chloride, acid, amino acid, or sulfonic acid. When $R_1$ is the same as $R_2$, a product in which primary and secondary hydroxyl groups are both esterified can be obtained through a one-step reaction by increasing the amount of a reagent.

Example 1: Preparation of Compound 1

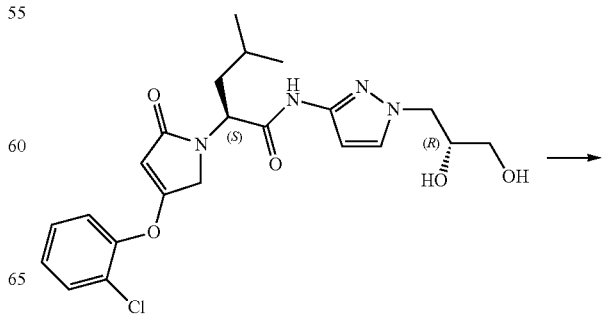

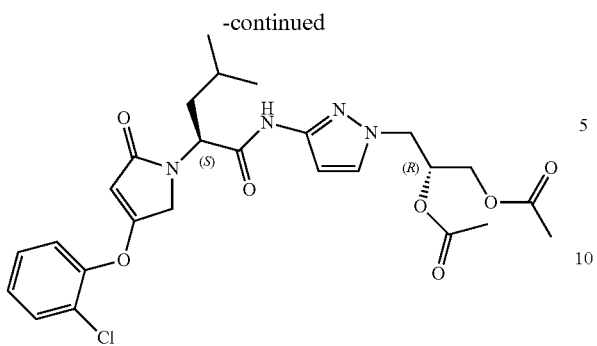

Synthetic Steps:

6 g (13 mmol, 1.0 eq.) of compound HMS5552 was dissolved in 20 mL of pyridine, and 16 mL (168 mmol, 13 eq.) of acetic anhydride was added dropwise. The reaction mixture was stirred at 20° C. for 18 h. The reaction mixture was quenched by adding water, and extracted twice with ethyl acetate. The organic phases were combined, washed sequentially with saturated aqueous citric acid, saturated aqueous sodium bicarbonate and saturated brine, then dried over anhydrous magnesium sulfate, and filtered. The filtrate was concentrated to dryness to give 6 g of Compound 1 (84.6% yield, bright yellow solid).

MS[M+H]$^+$: 547.18; $^1$H-NMR (d$^6$-DMSO, 400 MHz): δ 10.85 (s, 1H), 7.52-7.67 (m, o, 2H), 7.45-7.49 (m, 2H), 7.35-7.39 (m, 1H), 6.46 (d, J=1.48, 1H), 5.25-5.30 (m, 1H), 4.89-4.93 (m, 1H), 4.80 (s, 1H), 4.59-4.64 (d, J=18.48, 1H), 4.20-4.33 (m, o, 4H), 4.02-4.06 (m, 1H), 2.03 (s, 3H), 1.99 (s, 3H), 1.74-1.80 (m, 1H), 1.54-1.61 (m, 1H), 1.45-1.58 (m, 1H), 0.90-0.92 (d, J=6.48, 3H), 0.94-0.95 (d, J=6.4, 3H).

Example 2: Preparation of Compound 2

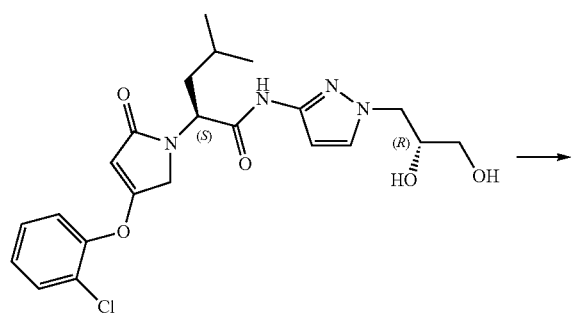

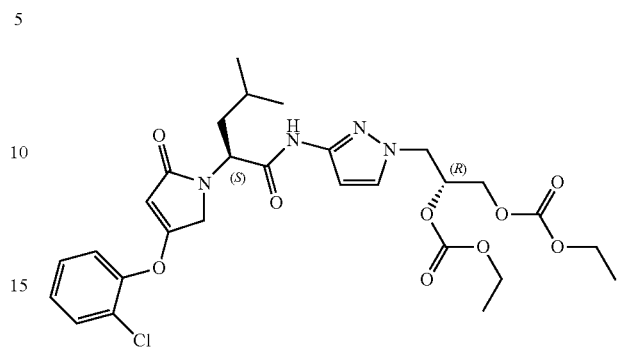

Synthetic Steps:

5.0 g (10.8 mmol, 1.0 eq.) of compound HMS5552 was dissolved in ethyl acetate, and 6.8 g (86 mmol, 8.0 eq.) of pyridine and 4.7 g (43.3 mmol, 4.0 eq.) of ethyl chloroformate were added at 0° C. The reaction mixture was stirred at room temperature for 20 h. The reaction mixture was quenched by adding water and the product was extracted twice with ethyl acetate. The organic phases were combined, washed with saturated brine, and concentrated to dryness. The residue was purified by preparative chromatography to give 4.5 g of Compound 2 (68.6% yield, white powder).

MS[M+H]$^+$: 607.18; $^1$H-NMR (d$^6$-DMSO, 400 MHz): δ 10.87 (s, 1H), 7.60-7.67 (m, 2H), 7.45-7.54 (m, 2H), 7.35-7.39 (m, 1H), 6.47 (s, 1H), 5.15-5.25 (m, 1H), 4.89-4.93 (dd, J1=10.80, J2=4.56, 1H), 4.79 (s, 1H), 4.59-4.64 (d, J=18.44, 1H), 4.24-4.39 (m, o, 4H), 4.06-4.19 (m, 5H), 1.70-1.82 (m, 1H), 1.52-1.62 (m, 1H), 1.35-1.50 (m, 1H), 1.16-1.23 (o, 6H), 0.94-0.95 (d, J=6.48, 3H), 0.90-0.92 (d, J=6.36, 3H).

Example 3: Preparation of Compound 3

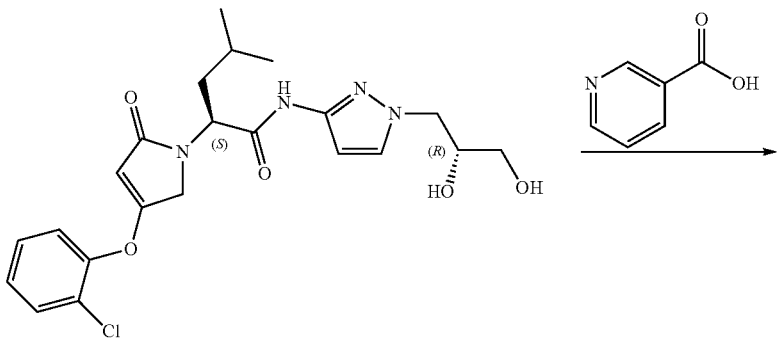

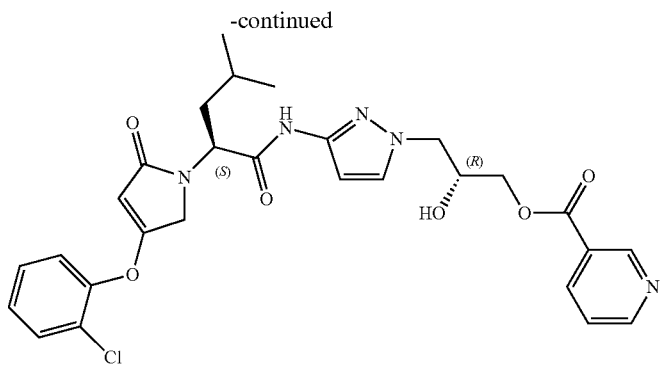

Synthetic Steps:

1.73 g (14.1 mmol, 1.3 eq.) of nicotinic acid was dissolved in DMF, and 4.19 g (32.4 mmol, 3.0 eq.) of diisopropylethylamine and 5.34 g of HATU (14.0 mmol, 1.3 eq.) were added at 0° C. The reaction mixture was stirred at 0° C. for 30 min, and then 5.0 g (10.8 mmol, 1.0 eq.) of compound HMS5552 was added in batches. The reaction was stirred at room temperature for 20 h. The reaction mixture was quenched by adding water, and extracted three times with ethyl acetate. The organic phases were combined, washed with saturated brine, dried over anhydrous magnesium sulfate, and filtered. The filtrate was concentrated and the residue was purified by preparative chromatography to give 3.3 g of Compound 3 (53.7% yield, pink brown solid).

MS[M+H]$^+$: 568.11; $^1$H-NMR (d$^6$-DMSO, 400 MHz): δ 10.81 (s, 1H), 9.16 (s, 1H), 8.82-8.84 (d, J=4.52, 1H), 8.32-8.34 (d, J=8.00, 1H), 7.62-7.66 (t, J=8.78, 2H), 7.57-7.60 (dd, J1=7.88, J2=4.68, 1H), 7.52-7.54 (d, J=8.04, 1H), 7.45-7.49 (t, J=7.72, 1H), 7.35-7.39 (t, J=7.62, 1H), 6.45 (s, 1H), 5.40-5.60 (br, 1H), 4.89-4.92 (dd, J1=10.60, J2=4.72, 1H), 4.80 (s, 1H), 4.60-4.64 (d, J=18.44, 1H), 4.012-4.29 (m, 6H), 1.68-1.80 (m, 1H), 1.48-1.62 (m, 1H), 1.32-1.50 (m, 1H), 0.94-0.95 (d, J=6.52, 3H), 0.90-0.92 (d, J=6.52, 3H).

Example 4: Preparation of Compound 4

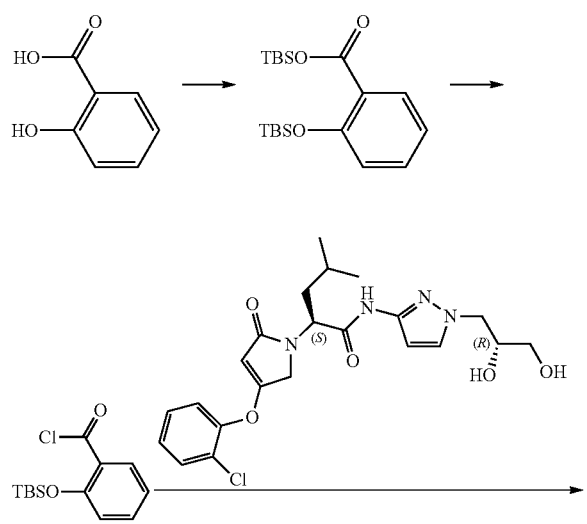

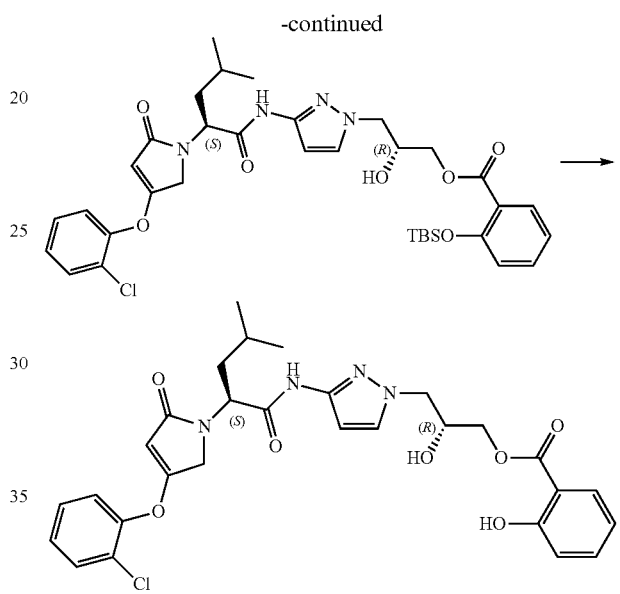

Synthetic Steps:

10.0 g (72.4 mmol, 1.0 eq.) of 2-hydroxybenzoic acid was dissolved in DMF, and 14.8 g (217.4 mmol, 3.0 eq.) of imidazole and 24.0 g (159.2 mmol, 2.2 eq.) of TBSCl were added respectively at 0° C. The reaction mixture was stirred at room temperature for 18 h. The reaction mixture was quenched by adding water and extracted twice with MTBE. The organic phases were combined, washed with saturated brine, dried over anhydrous magnesium sulfate, and filtered. The filtrate was concentrated to dryness to give 27 g of tert-butyldimethylsilyl 2-((tert-butyldimethylsilyl)oxy)benzoate, 101.7% crude yield.

12 g (32.7 mmol, 1.0 eq.) of tert-butyldimethylsilyl 2-((tert-butyldimethylsilyl)oxy)benzoate was dissolved in dichloromethane, and four drops of DMF were added. 4.8 g (37.8 mmol, 1.2 eq.) of oxalyl chloride was added dropwise at 0° C. and the reaction was stirred at room temperature for 18 h. The reaction mixture was quenched with methanol, and then concentrated to dryness to give 8.2 g of 2-((tert-butyldimethylsilyl)oxy)benzoyl chloride, 92.5% crude yield.

6.0 g (13.0 mmol, 1.0 eq.) of compound HMS5552 was dissolved in ethyl acetate, and 4.1 g (51.8 mmol, 4.0 eq.) of pyridine was added at 0° C., and then 5.27 g (19.5 mmol, 1.5 eq.) of 2-((tert-butyldimethylsilyl)oxy)benzoyl chloride was added dropwise. The reaction mixture was stirred at room temperature for 18 h. The reaction mixture was quenched by adding water, and extracted twice with ethyl acetate. The organic phases were combined, washed with saturated brine and concentrated to dryness. The residue was purified by preparative chromatography to give 5.5 g of (R)-3-(3-((S)-2-(4-(2-chlorophenoxy)-2-oxo-2,5-dihydro-1H-pyrrol-1-yl)-4-methylpentanamido)-1H-pyrazol-1-yl)-2-hydroxypropyl 2-((tert-butyldimethylsilyl)oxy)benzoate, 60.8% yield.

5.5 g (7.89 mmol, 1.0 eq.) of (R)-3-(3-((S)-2-(4-(2-chlorophenoxy)-2-oxo-2,5-dihydro-1H-pyrrol-1-yl)-4-methylpentanamido)-1H-pyrazol-1-yl)-2-hydroxypropyl 2-((tert-butyldimethylsilyl)oxy)benzoate was dissolved in tetrahydrofuran, and 9 mL of 1M solution of TBAF (9 mmol, 1.14 eq.) in tetrahydrofuran was added dropwise at 0° C. The reaction was stirred at room temperature for 6 h. The reaction was quenched by adding water and the product was extracted three times with ethyl acetate. The organic phases were combined, washed with saturated brine, and concentrated to dryness. The residue was purified by reversed-phase preparative chromatography to give 1.0 g of Compound 4 (21.7% yield, white powder).

MS[M+H]$^+$: 583.06; $^1$H-NMR (d$^6$-DMSO, 400 MHz): δ 10.84 (s, 1H), 10.49 (s, 1H), 7.25-8.05 (m, o, 7H), 6.80-7.15 (m, 2H), 6.30-6.60 (m, 1H), 5.55 (s, 1H), 4.50-5.05 (m, 3H), 3.95-4.65 (m, 6H), 1.30-1.75 (m, 3H), 0.70-0.95 (m, 6H).

Example 5: Preparation of Compound 5

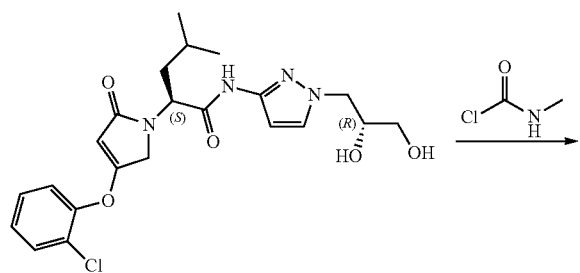

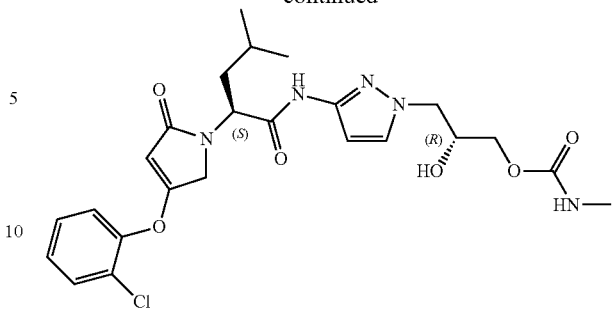

Synthetic Steps:

6.0 g (13.0 mmol, 1.0 eq.) of compound HMS5552 was dissolved in a mixture of 45 mL of THF and 45 mL of pyridine, and 24.24 g (259 mmol, 20 eq.) of N-methylchloroformamide was added at −10° C. in batches. The reaction mixture was stirred at room temperature for 20 h. The reaction mixture was quenched by adding water, and extracted twice with ethyl acetate. The organic phases were combined, washed with saturated brine and concentrated to dryness. The residue was purified by preparative chromatography to give 2.5 g of Compound 5 (37.1% yield, white powder).

MS[M+H]$^+$: 520.12; $^1$H-NMR (d$^6$-DMSO, 400 MHz): δ 10.82 (s, 1H), 7.65-7.67 (m, 1H), 7.45-7.54 (m, 3H), 7.35-7.37 (m, 1H), 7.04-7.05 (m, 1H), 6.43 (s, 1H), 5.26 (br, 1H), 4.91-4.92 (m, 1H), 4.80 (s, 1H), 4.60-4.64 (d, J=18.44, 1H), 4.19-4.24 (d, J=18.44, 1H), 3.87-4.07 (m, 4H), 2.51 (s, 3H), 2.08 (s, 1H), 1.73-1.80 (m, 1H), 1.54-1.61 (m, 1H), 1.40-1.49 (m, 1H), 0.94-0.95 (d, J=6.52, 3H), 0.90-0.92 (d, J=6.32, 3H).

Example 6: Preparation of Compound 6 and Citrate Salt Thereof

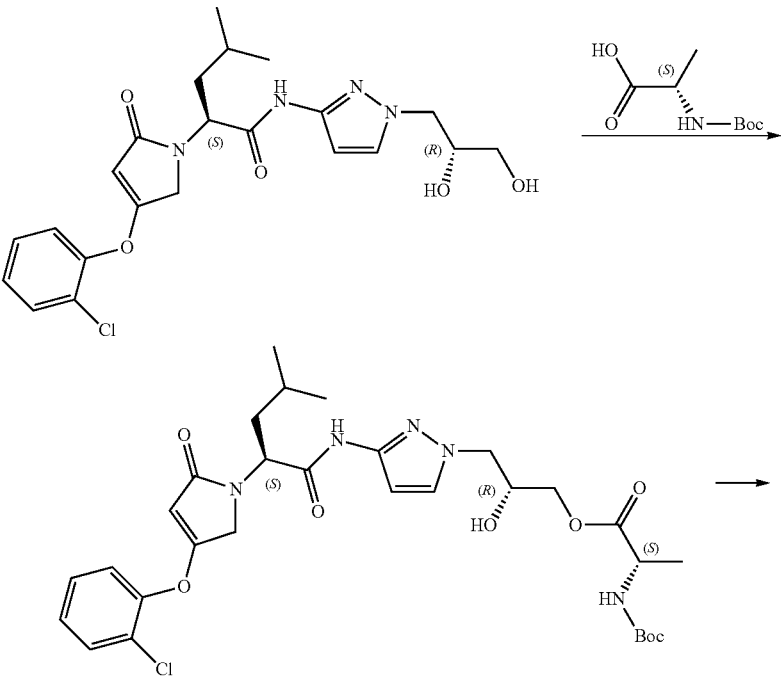

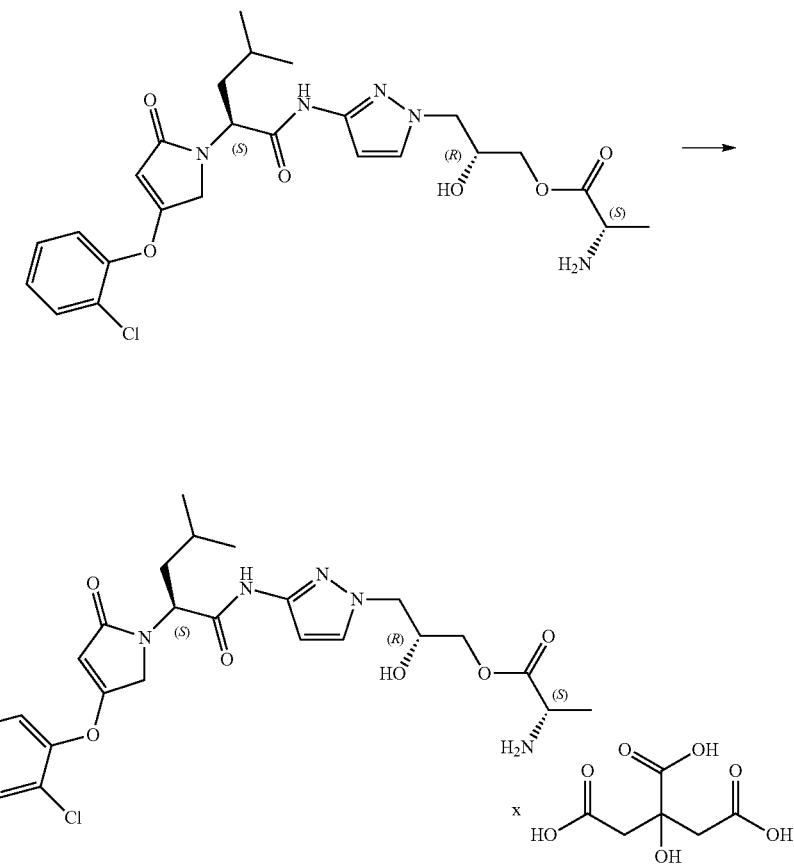

Synthetic Steps:

4 g (21 mmol, 1.4 eq.) of (S)-2-((tert-butoxycarbonyl)amino)propionic acid was dissolved in DMF, and 7.8 g (60.3 mmol, 4.0 eq.) of diisopropylethylamine and 8.1 g (21.3 mmol, 1.4 eq.) of HATU were added at 0° C. The mixture was stirred for 30 min, and then 7.0 g (15.1 mmol, 1.0 eq.) of HMS5552 was added in batches. The reaction mixture was stirred at room temperature for 20 h. The reaction mixture was quenched by adding water, and extracted three times with ethyl acetate. The organic phases were combined, washed with saturated brine, dried over anhydrous magnesium sulfate, and filtered. The filtrate was concentrated to dryness. The residue was purified by preparative chromatography to give 5.3 g of (R)-3-(3-((S)-2-(4-(2-chlorophenoxy)-2-oxo-2,5-dihydro-1H-pyrrol-1-yl)-4-methylpentanamido)-1H-pyrazol-1-yl)-2-hydroxypropyl (S)-2-((tert-butoxycarbonyl)amino)propionate (55.3% yield).

5.3 g (8.4 mmol, 1.0 eq.) of (R)-3-(3-((S)-2-(4-(2-chlorophenoxy)-2-oxo-2,5-dihydro-1H-pyrrol-1-yl)-4-methylpentanamido)-1H-pyrazol-1-yl)-2-hydroxypropyl (S)-2-((tert-butoxycarbonyl)amino)propionate was dissolved in dichloromethane, and 20 mL of trifluoroacetic acid was added at 0° C. The reaction was stirred at room temperature for 4 h. The reaction solution was concentrated to dryness and the residue was adjusted to a pH of 8-9 with saturated sodium carbonate. The product was extracted with dichloromethane and concentrated to dryness to give 4.2 g of Compound 6 (94.1% yield, white powder).

MS[M+H]$^+$: 534.11; $^1$H-NMR (d$^6$-DMSO, 400 MHz): δ 10.81 (s, 1H), 7.65-7.67 (m, 1H), 7.45-7.58 (m, o, 3H), 7.36-7.39 (m, 1H), 6.43 (s, 1H), 5.37 (s, 1H), 4.88-4.92 (m, 1H), 4.79 (s, 1H), 4.59-4.64 (d, J=18.44, 1H), 4.19-4.24 (d, J=18.44, 1H), 3.90-4.19 (m, 4H), 3.35-3.43 (m, 1H), 1.90-2.10 (m, 1H), 1.73-1.80 (m, 1H), 1.54-1.61 (m, 1H), 1.45-1.46 (m, 1H), 1.17-1.19 (d, J=6.92, 3H), 0.94-0.95 (d, J=6.52, 3H), 0.90-0.92 (d, J=6.40, 3H).

Citrate Salt of Compound 6

4.2 g (7.9 mmol, 1.0 eq.) of Compound 6 was dissolved in 50 mL of THF and a solution of 604 mg (3.14 mmol, 0.4 eq.) of citric acid in THF (20 mL) was added dropwise at 0° C. The reaction solution was stirred at 0° C. for 1 h. The reaction solution was concentrated to dryness, and then 30 mL of ethyl acetate was added to the concentrate to give a clear solution. Then 60 mL of MTBE was added slowly, and a large amount of solid was precipitated out. The mixture was filtered. The solid was recrystallized with ethyl acetate/MTBE to give 3.4 g of citrate salt of Compound 6 with a purity of 95.0% by HPLC. [MS[M+H]$^+$: 534.11]

Example 7: Preparation of Compound 7 and Citrate Salt Thereof

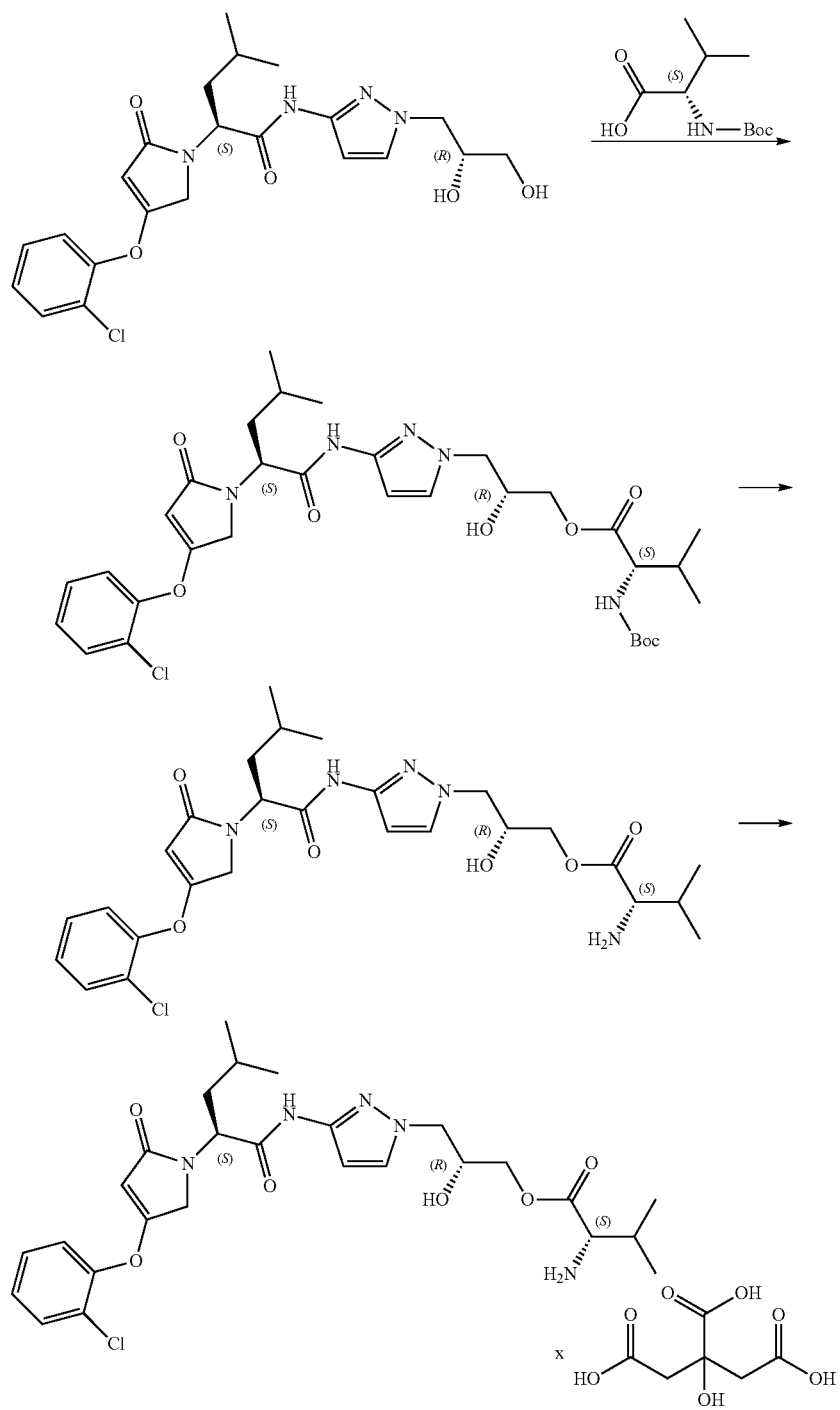

Synthetic Steps:

3.7 g (17 mmol, 1.3 eq.) of (S)-2-((tert-butoxycarbonyl)amino)-3-methylbutanoic acid was dissolved in DMVF, and 5.0 g (38.7 mmol, 3.0 eq.) of diisopropyl ethyl amine and 6.4 g (16.8 mmol, 1.3 eq.) of HATU were added at 0° C. The mixture was stirred at room temperature for 30 min, and then 6.0 g (13.0 mmol, 1.0 eq.) of compound HMS5552 was added in batches. The reaction was stirred at room temperature for 18 h. The reaction mixture was quenched by adding water, and extracted three times with ethyl acetate. The organic phases were combined, washed with saturated brine, dried over anhydrous magnesium sulfate, and filtered. The filtrate was concentrated and the residue was purified by preparative chromatography to give 3.9 g of (R)-3-(3-((S)-

2-(4-(2-chlorophenoxy)-2-oxo-2,5-dihydro-1H-pyrrol-1-yl)-4-methylpentanamido)-1H-pyrazol-1-yl)-2-hydroxypropyl (S)-2-((tert-butoxycarbonyl)amino)-3-methyl butyrate (45.4% yield).

3.9 g (5.9 mmol, 1.0 eq.) of (R)-3-(3-((S)-2-(4-(2-chlorophenoxy)-2-oxo-2,5-dihydro-1H-pyrrol-1-yl)-4-methylpentanamido)-1H-pyrazol-1-yl)-2-hydroxypropyl (S)-2-((tert-butoxycarbonyl)amino)-3-methyl butyrate was dissolved in dichloromethane. 13 mL of trifluoroacetic acid was added at 0° C. The reaction mixture was stirred at room temperature for 4 h. The reaction solution was concentrated to dryness, and the residue was adjusted to a pH of 8-9 with saturated sodium carbonate. The product was extracted with dichloromethane and concentrated to dryness to give 2.7 g of Compound 7 (81.6% yield, white powder).

MS[M+H]$^+$: 562.29; $^1$H-NMR (d$^6$-DMSO, 400 MHz): δ 10.80 (s, 1H), 7.65-7.67 (m, 1H), 7.47-7.57 (m, o, 3H), 7.35-7.35 (m, 1H), 6.43-6.44 (d, J=5.48, 1H), 5.35 (s, 1H), 4.92-4.93 (m, 1H), 4.89 (s, 1H), 4.59-4.64 (d, J=18.48, 1H), 4.19-4.27 (o, 2H), 3.90-4.10 (m, 4H), 3.13-3.14 (d, J=5.32, 1H), 1.45-1.89 (m, o, 6H), 0.77-0.95 (o, 12H).

Citrate salt of Compound 7

2.3 g (4.1 mmol, 1.0 eq.) of Compound 7 was dissolved in 30 mL of tetrahydrofuran, and a solution of 314 mg (1.63 mmol, 0.4 eq.) of citric acid in THF (10 mL) was added dropwise at 0° C. The reaction solution was stirred at 0° C. for 1 h and then concentrated to dryness. To the concentrate, 20 mL of ethyl acetate was added to give a clear solution. 40 mL of methyl tert-butyl ether was then slowly added, and the product was precipitated. The precipitate was filtered and dried to give 2.1 g of the citrate salt of Compound 7 with a purity of 94.8% by HPLC. [MS[M+H]$^+$: 562.29]

Example 8: Preparation of Compound 8

6.0 g (13.0 mmol, 1.0 eq.) of compound HMS5552 was dissolved in dichloromethane, and 493 mg (2.9 mmol, 0.22 eq.) of p-toluenesulfonic acid was added at 0° C. 4.6 g (38.9 mmol, 3.0 eq.) of acetaldehyde diethyl acetal was then added dropwise. The reaction mixture was stirred at room temperature for 96 h. The reaction solution was concentrated to dryness and the crude product was purified by preparative chromatography to give 4.0 g of Compound 8 (63.1% yield, white powder).

MS[M+H]$^+$: 489.05; $^1$H-NMR (d$^6$-DMSO, 400 MHz): δ 10.83 (s, 1H), 7.62-7.67 (m, 2H), 7.45-7.54 (m, 2H), 7.35-7.39 (m, 1H), 6.45-6.46 (d, J=1.88, 1H), 4.90-4.98 (m, 2H), 4.80 (s, 1H), 4.60-4.64 (d, J=18.48, 1H), 4.33-4.35 (m, 1H), 4.24-4.20 (d, J=18.48, 1H), 4.09-4.16 (m, 2H), 3.80-3.84 (m, 2H), 1.73-1.80 (m, 1H), 1.54-1.61 (m, 1H), 1.40-1.49 (m, 1H), 1.22-1.27 (dd, J=13.70, J=4.74, 3H), 0.94-0.95 (d, J=6.52, 3H), 0.90-0.92 (d, J=6.32, 3H)

Example 9: Stability Test of Compounds in Simulated Gastric Fluid (SGF)

Preparation of Simulated Gastric Fluid (SGF): Dissolve 0.04 g NaCl and 0.064 g pepsin in 0.14 mL HCl and add sufficient H$_2$O to make the final volume to 20 mL. The pH of the test solution was about 1.20±0.05.

Preparation of test compound working solutions: Spike 5 μL of 30 mM test compound stock solution to 745 μL of DMSO to yield 200 μM test compound working solution.

1) Spike 2 μL of 200 μM test compound working solution into corresponding wells of T0, T60, T120, T360, and T1440 (Duplicate were prepared, n=2) of 96-deep-well plates.
2) Transfer 198 μL of SGF solution to the above corresponding wells except T0 to reach 2 μM as final test compound concentration for each time point (60, 120,

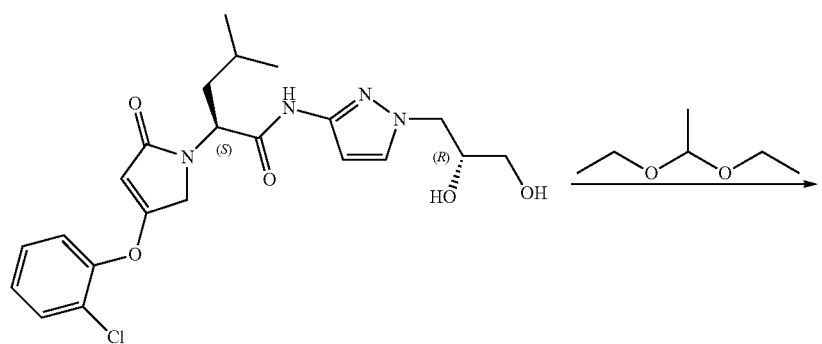

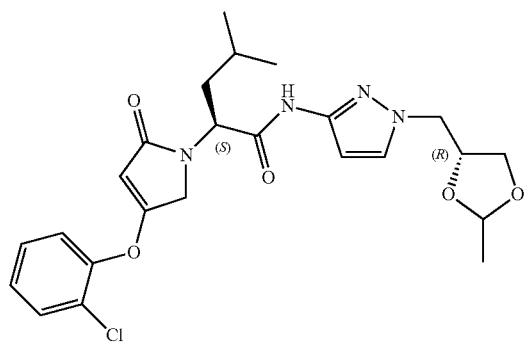

360, and 1440 minutes). The final concentration of DMSO in the incubation mixture was 1%.
3) Incubate samples at 37° C., 600 rpm for the appointed time.
4) Samples at corresponding time point (60, 120, 360, and 1440 minutes) were removed at the end of incubation time and immediately mixed completely with 400 μL of cold acetonitrile containing 200 ng/mL tolbutamide (internal standard).
5) 200 μL of supernatant was removed and mixed completely again with 400 μL of cold acetonitrile containing 200 ng/mL tolbutamide (internal standard).
6) Preparation of the T0 samples: Transfer 198 μL of SGF solution to corresponding well after adding 400 μL of cold acetonitrile containing 200 ng/mL tolbutamide (internal standard), and mixed completely. Then 200 μL of supernatant was pipetted and mixed completely again with 400 μL of cold acetonitrile containing 200 ng/mL tolbutamide (internal standard).
7) All samples were centrifuged at 4000 rpm, 4° C. for 20 min.
8) 60 μL of supernatant was pipetted and mixed with 180 μL of ultra-pure water, and the mixture was mixed completely for LC-MS/MS analysis.

The concentrations of the test compounds and the converted compound HMS5552 were measured, and the remaining/generation rate versus incubation time were plotted to evaluate the stability of the test compounds in simulated gastric fluid (SGF).

LC-MS/MS Condition:
LC: Shimadzu LC 30-AD,
MS: QTRAP 6500+,
Autosampler: CTC PAL,
Mobile Phase: A: 0.1% Formic Acid in Water, B: 0.1% Formic Acid in Acetonitrile,
Column: ACQUITY UPLC Protein BEH C4 300 Å 2.1*50 mm Part No. 186004495,
Total Flow: 600 μL/min,
Scan Type: multiple reaction monitoring (MRM).
The results are shown in Table 2, FIG. 1 and FIG. 2.

TABLE 2

Stability data of test compounds in Simulated Gastric Fluid

| Compound ID | Time Point (hr) | Remaining of Test Compound (%) | Parent Drug HMS5552 (%) |
|---|---|---|---|
| Compound 3 | 0 | 100.00 | 0.92 |
|  | 1 | 90.35 | 0.86 |
|  | 2 | 95.99 | 0.87 |
|  | 6 | 90.10 | 1.02 |
|  | 24 | 89.48 | 1.63 |
| Compound 7 | 0 | 100.00 | 0.39 |
|  | 1 | 103.14 | 0.44 |
|  | 2 | 104.44 | 0.53 |
|  | 6 | 102.68 | 0.49 |
|  | 24 | 108.07 | 0.72 |

Figure 2:
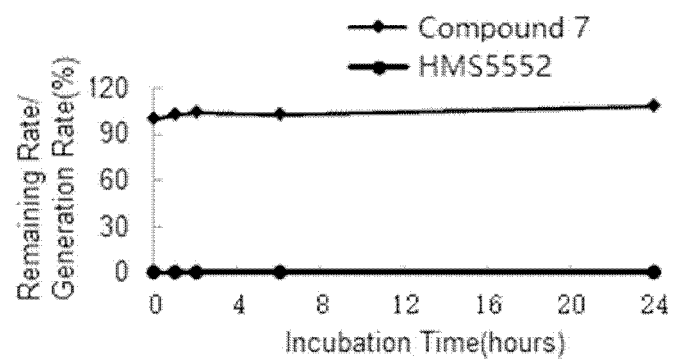
FIG. 2 is a graph showing the comparison of remaining rate/generation rate-incubation time of compound 7 and HMS5552 in artificial simulated gastric fluid.

The results in Table 2, FIG. 1 and FIG. 2 show that Compound 3 and Compound 7 were stable in SGF for 24 hours, and both only slightly degraded into the parent drug HMS5552.

Example 10: Stability Test of Compounds in Simulated Intestinal Fluid (SIF)

Preparation of Simulated Intestinal Fluid (SIF): Dissolve 0.136 g $KH_2PO_4$ and 0.2 g pancreatin with water and make up the final volume to 20 mL. The pH of the test solution was about 6.80±0.05.

Preparation of test compound working solution: Spike 10 μL of 10 mM test compound stock solution to 490 μL of DMSO to yield 200 μM test compound working solution.

1) Spike 2 μL of 200 μM working solution into corresponding wells of T0, T60, T120, T360, and T1440 (Duplicate were prepared, n=2) of 96-deep-well plates.
2) Transfer 198 μL of SIF solution to above corresponding wells except T0 to reach 2 μM as final test compound concentration for each time point (60, 120, 360, and 1440 minutes). The final concentration of DMSO in the incubation mixture was 1%.
3) Incubate samples at 37° C., 600 rpm for the appointed time.
4) Samples at corresponding time point (60, 120, 360, and 1440 minutes) were removed at the end of incubation time and immediately mixed completely with 400 μL of cold acetonitrile containing 200 ng/mL tolbutamide (internal standard).
5) 200 μL of supernatant was removed and mixed completely again with 400 μL of cold acetonitrile containing 200 ng/mL tolbutamide (internal standard).
6) Preparation of the T0 samples: Transfer 198 μL of SIF solution to corresponding well after adding 400 μL of cold acetonitrile containing 200 ng/mL tolbutamide (internal standard), and mixed completely. Then 200 μL of supernatant was pipetted and mixed completely again with 400 μL of cold acetonitrile containing 200 ng/mL tolbutamide (internal standard).
7) All samples were centrifuged at 4000 rpm, 4° C. for 20 min.
8) 60 μL of supernatant was pipetted and mixed with 180 μL of ultra-pure water, and the mixture was mixed completely for LC-MS/MS analysis.

The concentrations of the test compounds and the converted compound HMS5552 were measured, and the remaining/generation rate versus incubation time were plotted to evaluate the stability of the test compounds in simulated intestinal fluid (SIF).

LC-MS/MS Condition:
LC: Shimadzu LC 30-AD,
MS: API4000,
Autosampler: CTC PAL,
Mobile Phase: A: 0.1% Formic Acid in Water, B: 0.1% Formic Acid in Acetonitrile,
Column: ACQUITYUPLC BEH C18 1.7 μm 2.1×50 mm Part No. 186002350,
Scan Type: multiple reaction monitoring (MRM).
The results are shown in Table 3, FIG. 3 and FIG. 4.

TABLE 3

Stability data of test compounds in Simulated Intestinal Fluid

| Compound ID | Time Point (hr) | Remaining of Test Compound (%) | Parent Drug HMS5552(%) |
|---|---|---|---|
| Compound 3 | 0 | 100.00 | 0.86 |
|  | 1 | 53.14 | 35.61 |
|  | 2 | 37.56 | 46.64 |
|  | 6 | 2.35 | 72.79 |
|  | 24 | 0.00 | 73.43 |
| Compound 7 | 0 | 100.00 | 2.36 |
|  | 1 | 25.13 | 73.25 |
|  | 2 | 3.50 | 97.05 |
|  | 6 | 4.88 | 98.51 |
|  | 24 | 0.00 | 103.39 |

Figure 3:
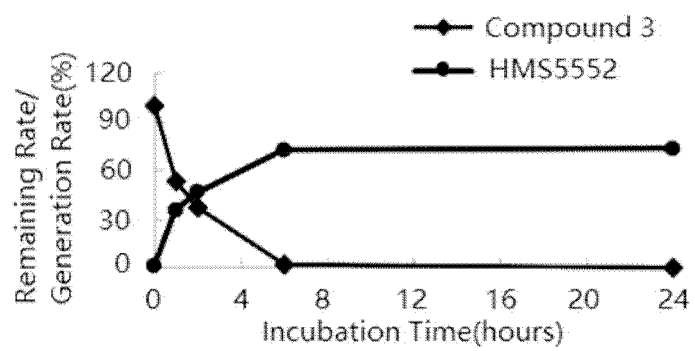
FIG. 3 is a graph showing the comparison of remaining rate/generation rate-incubation time of compound 3 and HMS5552 in artificial simulated intestinal fluid.
Figure 4:
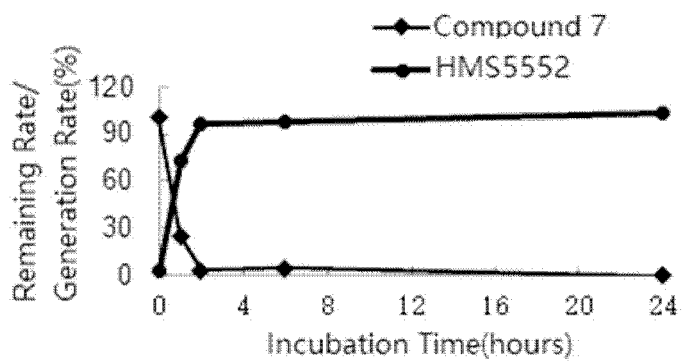
FIG. 4 is a graph showing the comparison of remaining rate/generation rate-incubation time of compound 7 and HMS5552 in artificial simulated intestinal fluid.

The results in Table 3, FIG. 3 and FIG. 4 show that Compound 3 and Compound 7 were extensively degraded in SIF, and most of them was converted to HMS15552.

Example 11: Simulated Metabolic Test of Compounds in Human Intestine S9

Preparation of Phosphate Buffer (PB): Dissolve 73.21 g $K_2TIPO_4 \cdot 3H_2O$ (AR grade) and 10.78 g $KH_2PO_4$ (AR grade) in ultra-pure water to make the final volume to 4000 mL and the final concentration to 100 mM. The pH of the final test solution was adjusted to pH 7.40±0.10 with $H_3PO_4$/KOH.

Preparation of test compound working solution: 5 μL of test compound stock solution (10 mM in DMSO) were diluted with 995 μL of acetonitrile (ACN) to give a test compound working solution (intermediate solution concentration: 50 mM, 990 ACN)

The main materials of the test are shown in Table 4, and the parameters of preparation components of human intestinal S9 (HIS9) solution are shown in Table 5.

TABLE 4

Main materials of the test

| Materials | Product information | Source |
|---|---|---|
| HumanIS9(HIS9) | Cat. No. H0610.IS9(NP) Lot No. 1710039 | Xenotech |
| D-glucaric acid-1,4-lactone (100 mM) | S0375 | Sigma |

TABLE 5

The parameters of preparation components of human intestinal S9 solution

| Components of human intestinal S9 mixture | Volume(μL) | Concentration of test compound working solution | Final concentration |
|---|---|---|---|
| HIS9 (4 mg-protein/mL) | 675 | 1.0 mg/mL | 0.5 mg/mL |
| D-glucaric acid-1,4-lactone (100 mM) | 270 | 10 mM | 5 mM |
| 100 mM PB | 1755 | — | — |
| Total volume | 2700 | — | — |

An Apricot automation workstation was used to add 50 μL/well of HIS9 solution to the corresponding wells of all reaction plates (blank, T0, T5, T15, T30, T45, T60).

Using an Apricot automation workstation, 2 μL/well of test compound working solution was added to the corresponding wells of all 96-well reaction plates except the blank (T0, T5, T15, T30, T45, T60).

An Apricot automation workstation was used to add 48 μL/well of PB to the corresponding wells of every reaction plate (Blank, T0, T5, T15, T30, T45, T60) to start the reaction.

The reaction plates were incubated at 37° C., and timer was started. An Apricot automation workstation was used to add 300 μL/well of stop solution (cold acetonitrile containing 200 ng/mL tolbutamide (internal standard)) to the corresponding wells of each reaction plate at its appropriate end time point to terminate the reaction.

Each plate was sealed and shaken for 10 minutes. After shaking, each plate was centrifuged at 4000 rpm and 4° C. for 20 minutes. After centrifugation, 100 μL of supernatant was transferred from each reaction plate to its corresponding bioanaylsis plate, and mixed well with 300 μL ultra-pure water.

Each bioanaylsis plate was sealed for LC-MS/MS analysis to obtain concentration of the test compounds and the converted compound HMS5552 so as to assess the metabolic transformation of test compound in Human Intestine S9.

LC-MS/MS Condition:
LC: Shimadzu LC 30-AD,
MS: API4000,
Autosampler: CTC PAL,
Mobile Phase: A: 0.1% Formic Acid in Water, B: 0.1% Formic Acid in Acetonitrile,
Column: ACQUITY UPLC BEH C18 1.7 m 2.1×50 mm Part No. 186002350, The results are shown in Table 6.

TABLE 6

Simulation results of test compound in human intestinal S9

| Compound ID | Time (min) Point | HIS9 Remaining of Test Compound (%) | Parent Drug HMS5552(%) |
|---|---|---|---|
| Compound 3 | 0 | 100 | 1.1 |
| | 5 | 0 | 80.0 |
| | 15 | 0 | 77.2 |
| | 30 | 0 | 79.8 |
| | 45 | 0 | 81.2 |
| | 60 | 0 | 90.5 |
| Compound 7 | 0 | 100 | 5.0 |
| | 5 | 30.7 | 64.6 |
| | 15 | 18.8 | 73.3 |
| | 30 | 7.2 | 76.1 |
| | 45 | 3.9 | 87.1 |
| | 60 | 2.7 | 103.0 |

Simulation results of human intestinal S9 in Table 6 show that Compound 3 and Compound 7 were well metabolized in human intestinal S9, and almost all of them were converted to parent drug HMS5552 within 60 minutes. Compound 3 was completely metabolized and converted into parent drug HMS5552 within 5 minutes.

Example 12: Test Using Caco-2 Cells to Bi-Directionally Assess the Permeability of Compound 3

Caco-2 cell culture: Caco-2 cells (Purchased from American Type Culture Collection, ATCC) were inoculated on polyethylene film (PET) of 96-well culture plate at a concentration of $1 \times 10^5$ cells/cm². The culture medium was replaced every 4 days until cell confluency to form cell monolayer on day 21 or 28.

Transport test: Transport Buffer used in the test was Hanks' Balanced Salt solution (HBSS) containing 10 mM 2-[4-(2-hydroxyethyl)-1-piperazinyl]ethanesulfonic acid (HEPES) at a pH of 7.40±0.05. In vitro permeability studies were performed with Nadolol, Metoprolol and digoxin as model permeants. Test compound 3 was assessed bi-directionally with test concentrations of 2.00, 10.0 and 30.0 μM (n=2), respectively. Digoxin was assessed bi-directionally with a test concentration of 10.0 M (n=2). Nadolol and Metoprolol were assessed unidirectionally with a test concentration of 2.00 μM (n=2). The final concentration of DMSO in the incubation system was adjusted to <1%.

Specific Steps:
1) The plate was incubated for 2 hours in $CO_2$ incubator at 37±1° C., with 5% $CO_2$ at saturated humidity without shaking.
2) At the end of incubation, all samples were mixed with acetonitrile containing internal standard, and centrifuged at 3200 g for 10 minutes.
3) For compound 3 in groups 10.0 μM and 30.0 M, T0 sample and the donor side sample were diluted 10 times with blank sample supernatant.
4) For Nadolol and Metoprolol, 200 μL supernatant was diluted with 600 uL ultra-pure water for LC-MS/MS analysis.
5) For Digoxin and test compound, 200 μL supernatant was diluted with 200 uL ultra-pure water for LC-MS/MS analysis.
6) The concentration of Compound 3, the parent drug HMS5552 and the control compound in the initial solution, the donor side solution, and the receiver side solution were quantitatively determined by the peak area ratio of the tested substance to the internal standard by LC-MS/MS.

Permeability test results of Compound are shown in Table 7.

TABLE 7

Permeability test results of Compound 3

| Compound 3 concentration (μM) | The average Apparent Permeability $P_{app}$ ($10^{-6}$ cm/s) | | Efflux Ratio | Average Recovery Rate (%) | | Average Conversion Rate to parent drug HMS5552 (%) | |
|---|---|---|---|---|---|---|---|
| | A→B | B→A | | A→B | B→A | A→B | B→A |
| 2.00 | 0.02977 | 11.9 | 401 | 52.9 | 87.1 | 26.55 | 5.8 |
| 10.0 | 0.03187 | 12.0 | 376 | 37.5 | 81.6 | 37.4 | 5.6 |
| 30.0 | 0.04322 | 11.9 | 276 | 37.6 | 82.2 | 26.8 | 3.4 |

Results in Table 7 show that the permeability of Compound 3 from A to B is low, while from B to A is high, which suggested that Compound 3 is likely to be the substrate for efflux transporters.

Example 13: Pharmacokinetic Studies

Eighteen male SD rats were divided into three groups by body weights (HMS5552 Group, Compound 3 Group and Compound 7 Group). Each group was divided into 2 subgroups (intravenous bolus group (IV) and gavage group (PO)). The intravenous bolus group (IV) was dosed 10 mg/kg HMS5552, 10 mg/kg Compound 3, or 10 mg/kg Compound 7 by a single intravenous bolus injection. The gavage group (PO) was dosed 30 mg/kg HMS5552, 30 mg/kg Compound 3, or 30 mg/kg Compound 7 by a single gavage.

Whole blood samples (about 0.2 mL per time point) were collected at pre-dose (0), 0.083, 0.25, 0.5, 1, 2, 4, 8, 12, and 24 hours post-dose by jugular vein puncture. All the blood samples were immediately transferred into labeled prechilled commercial microcentrifuge tubes containing 4 μL of 0.5M EDTA-$K_2$ and 10 μL of cocktail stabilizer. Samples were placed on wet ice until centrifugation (within 30 min). Plasma samples were then prepared by centrifuging the blood samples at approximately 4° C., 3200×g for 10 minutes. Supernatant plasma was pipetted, then quickly frozen over dry ice and kept at −60° C. or lower temperature until LC-MS/MS analysis.

The cocktail stabilizer was prepared according to the following Table 8:

TABLE 8

Cocktail stabilizer formula

| Cocktail stabilizer components | Stock concentration of components | Stock solvent | Volume | Conc. of components | Cocktail stabilizer to whole blood sample ratio | Final Conc. of components |
|---|---|---|---|---|---|---|
| Citric Acid | 600 mM | Water | 0.5 mL | 150 mM | 1:20 (v:v), e.g., 0.1 mL cocktail stabilizer + 2.0 mL whole blood | 7.5 mM |
| PMSF | 400 mM | DMSO | 0.5 mL | 100 mM | | 5 mM |
| NaF | 400 mM | Water | 0.5 mL | 100 mM | | 5 mM |
| Dichlorvos | 400 mM | Water | 0.5 mL | 100 mM | | 5 mM |

The plasma concentrations were subjected to a non-compartmental pharmacokinetic analysis by using the WinNonlin™ software program (version 6.3). The linear/log trapezoidal rule was applied in obtaining the PK parameters, and the results are shown in Table 9.

as the control group, other groups were administered with corresponding concentration of test compounds (5 mL/kg, PO). The low, middle, and high dose levels of Compound 3, Compound 6 and Compound 7 treatment groups are equivalent (equimolar) to 5, 15, and 40 mg/kg HMS5552 groups.

TABLE 9

Pharmacokinetic Results

| | group #1 (HMS5552) | | group #2 (Compound 3) | | | | group #3 (Compound 7) | | | |
|---|---|---|---|---|---|---|---|---|---|---|
| | IV (parent drug) | PO (parent drug) | IV (pro drug) | PO (prodrug) | IV (parent drug) | PO (parent drug) | IV (pro drug) | PO (pro drug) | IV (parent drug) | PO (parent drug) |
| $C_{max}$ (ng/ml) | / | 2459 | / | 0.973 | / | 1346 | / | 27.0 | / | 1973 |
| $C_{max}$ Ratio (%, Prodrug/Parent) | / | / | / | 0.07 | / | / | / | 1.4 | / | / |
| $C_{max}$ Ratio (%, Parent converted from prodrug/Parent in group#1) | / | / | / | / | / | 67.2** | / | / | / | 97.4** |
| $T_{max}$ (h)* | / | 1 [1-1] | / | 0.25 [0.25-0.25] | / | 1 [0.5-1] | / | 1 [0.083-2] | / | 2 [1-2] |
| $AUC_{0-last}$ (h · ng/mL) | 5049 | 7737 | 576 | 1.4 | 3422 | 5063 | 382 | 31.6 | 2993 | 6503 |
| $AUC_{inf}$ (h · ng/mL) | 5051 | 7758 | 577 | 2.05 | 3423 | 5069 | 383 | ND | 2997 | 6521 |
| AUC Ratio (%, Prodrug/Parent) | / | / | / | 0.04 | / | / | / | 0.5 | / | / |
| AUC Ratio (%, Parent converted from prodrug/Parent in group#1) | / | / | / | / | / | 80.2** | / | / | / | 102.1** |
| CL (mL/min/kg) | 33.1 | / | 290 | / | / | / | 437 | / | / | / |
| $V_d$ (L/kg) | 1.66 | / | 2.49 | / | / | / | 7.55 | / | / | / |
| $T_{1/2}$ (h)* | 3.51 | 3.34 | 0.33 | / | 3.59 | 2.63 | 1.64 | / | 4.34 | 3.25 |
| Bioavailability (%) | / | 51.2 | / | 0.08 | / | / | / | 2.8 | / | / |

*$T_{max}$ is median [Min, Max];
**converted based on molar (MW of HMS5552, Compound 3 and Compound 7 are 462.93, 568.03, and 562.06, respectively).

The results in Table 9 show that Compound 3 and Compound 7 are metabolized very rapidly in rats by intravenous injection. When administered orally, the exposures (Cmax, Cmax ratio, AUC, AUC ratio) of Compound 3 and Compound 7 were comparable to the parent drug HMS5552. The above study results show that Compound 3 and Compound 7 is metabolized in the gastrointestinal tract and enterocytes to HMIN/S5552, which is absorbed and then enters the circulatory system.

Example 14: Pharmacodynamics Study

To study the glucose-lowering effect of HMS5552, Compound 3, Compound 6 and Compound 7 in C57BL/6J mice.
Method
104 C57BL/6J mice were randomly divided into 13 groups according to body weight, 8 mice per group. The first group were administered with vehicle solvent (5 mL/kg, PO)

The oral glucose tolerance test (OGTT) was performed 1 hour after administration of test compounds. Blood glucose (BG) were measured at −60 min (pre-dose), 0 min (pre-glucose), 15 min, 30 min, 60 min and 120 min after glucose treatment. Blood samples (40 μl) were collected from tail veins at 0 min (pre-glucose), and 15 min (post-glucose) to separate plasma for insulin detection.

Data Processing and Analysis

All data was transferred into an Excel spreadsheet. Blood glucose was expressed in mg/dL. All values were expressed as Mean±SEM. The significance of the differences between groups were evaluated by one-way ANOVA or two-way ANOVA followed by Dunnett's multiple comparisons test or Tukey's multiple comparisons test using GraphPad Prism 8. A p value of less than 0.05 is considered statistically significant.

Results

Body weight (BW): During the experiment, the BW values of all groups are similar, no significant differences were found between groups.

Figure 5:
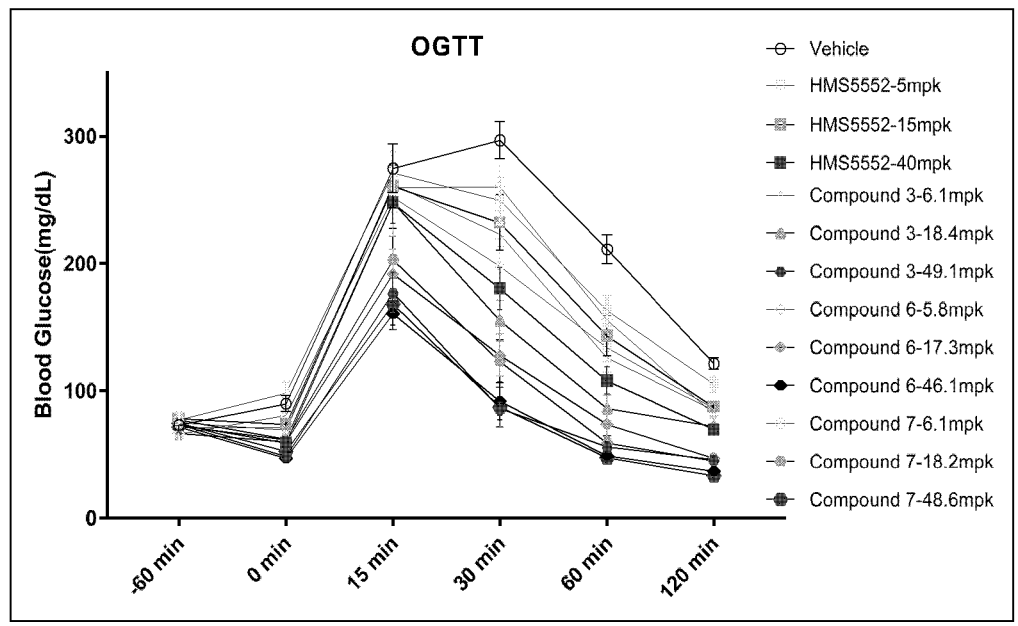
FIG. 5 is a graph showing the OGTT blood glucose-time curve, and $AUC_{0-120min}$ comparing HMS5552, Compound 3, Compound 6 and Compound 7 in C57BL/6J Mice. In the graph, * means P<0.05 and ** means P<0.01, as compared to the Vehicle control group; and # means P<0.05 and ## means P<0.01, as compared to the corresponding HMS5552 dosing group.
Figure 5:
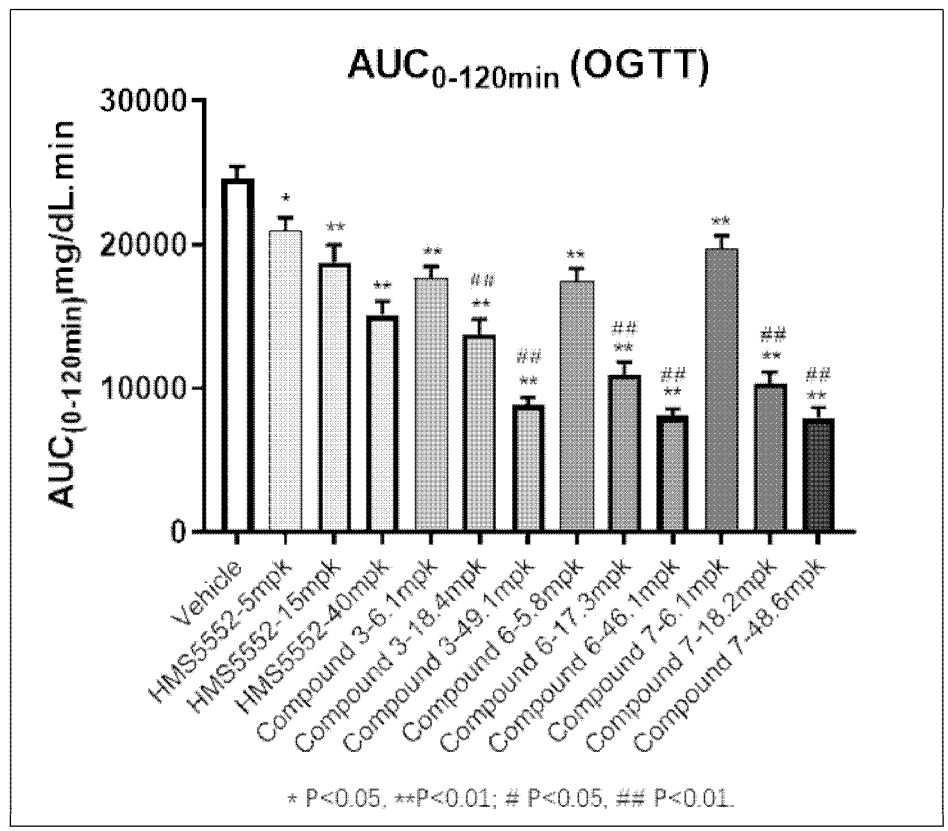

OGTT result is shown in FIG. 5. FIG. 5 shows that the BG values of all groups at −60 min (pre-dose) are similar, no significant differences were found between groups.

After treatment with HMS5552, Compound 3, Compound 6 and Compound 7, the BG values of all treatment groups at 0 min (pre-glucose) were overall lower than the vehicle control group, with dose-response relationship.

After glucose treatment, the BG values of each group were increased significantly.

The BG values of HMS5552-40 mg/kg group were significantly lower than the vehicle control group at 30 min, 60 min and 120 min. The BG values of Compound 3-49.1 mg/kg group were significantly lower than the vehicle control group at 15 min, 30 min, 60 min, and 120 min, and were significantly lower than HMS5552-40 mg/kg group at 30 min, 60 min, and 120 min. The BG values of Compound 6-46.1 mg/kg group, Compound 7-48.6 mg/kg group were significantly lower than HMS5552-40 mg/kg group at 15 min, 30 min, 60 min, and 120 min.

$AUC_{0-120min}$ of all low, middle, high dose groups of HMS5552, Compound 3, Compound 6, and Compound 7 were significantly lower than the vehicle control group, with dose-response relationship. $AUC_{0-120min}$ of Compound 3, Compound 6, and Compound 7 treatment groups at middle and high dose levels were significantly lower than the corresponding groups of HMS5552 (P<0.01).

OGTT result shows that all the test compounds showed good glucose-lowering effect in mice.

Figure 6:
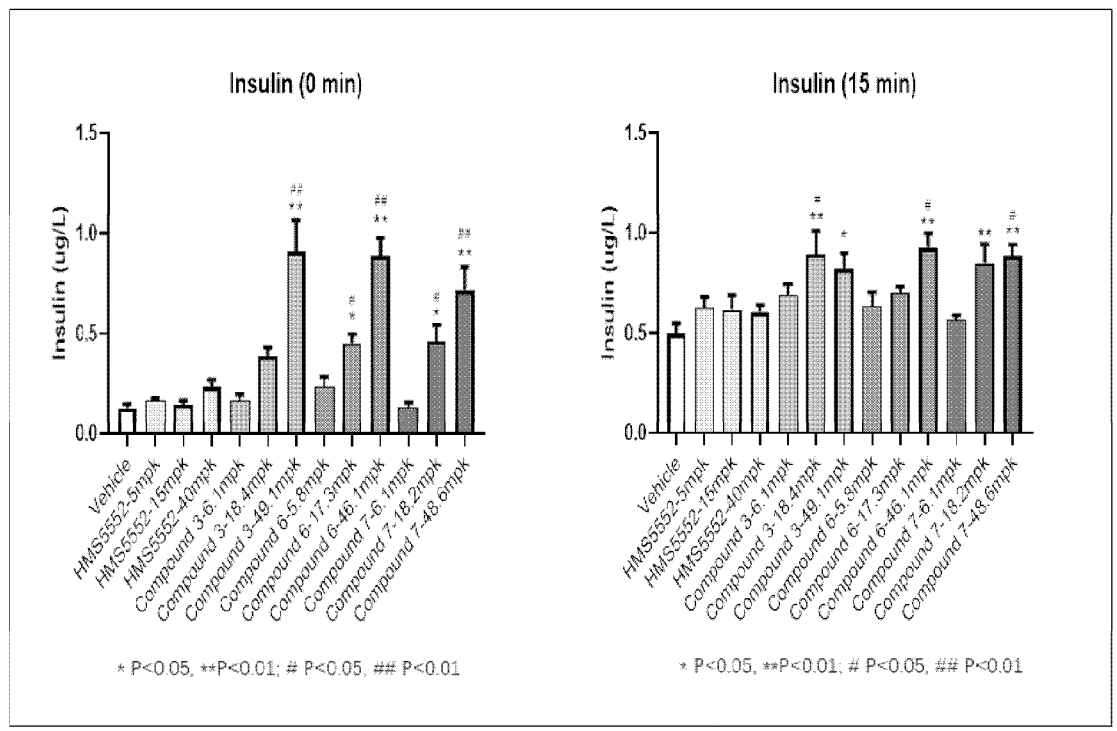
FIG. 6 is a graph showing the Insulin levels (0 min and 15 min) comparing HMS5552, Compound 3, Compound 6 and Compound 7 in C57BL/6J Mice. In the graph, * means P<0.05 and ** means P<0.01, as compared to the Vehicle control group; and # means P<0.05 and ## means P<0.01, as compared to the corresponding HMS5552 dosing group.

Insulin test result is shown in FIG. 6. FIG. 6 shows that the insulin levels of the vehicle control group were 0.13±0.02 (μg/L) at 0 min and 0.50±0.05 (μg/L) at 15 min. The insulin levels of HMS5552 groups were slightly higher than the vehicle control group at 0 min and 15 min, without significant difference. The insulin levels of Compound 3-49.1 mg/kg group, Compound 6-46.1 mg/kg group, and Compound 7-48.6 mg/kg group were significantly higher than the vehicle control group and HMS5552-40 mg/kg group at 0 min. The insulin levels of Compound 3-18.4 mg/kg group, Compound 3-49.1 mg/kg group, Compound 6-46.1 mg/kg group, Compound 7-18.2 mg/kg group, and Compound 7-48.6 mg/kg group were significantly higher than the vehicle control group at 15 min. The insulin levels of Compound 3-18.4 mg/kg group, Compound 6-46.1 mg/kg group, and Compound 7-48.6 mg/kg group were significantly higher than the corresponding groups of HMS5552 at 15 min.

This study shows that all the test compounds of the present invention have good glucose-lowering effect in C57BL/6J mice. Compound 3, Compound 6 and Compound 7 lead to increased insulin secretion and greater glucose-lowering effect as compared to HMS5552.

The above is a further detailed description of the present disclosure in connection with the specific alternative embodiments, and the specific embodiments of the present disclosure are not limited to the description. For those skilled in the art, without departing from the concept of the present invention, some simple deductions or substitutions can be made, which should be regarded as falling within the protection scope of the present invention.

What is claimed is:

1. A compound of formula (I), or an enantiomer, a diastereomer, or a pharmaceutically acceptable salt thereof:

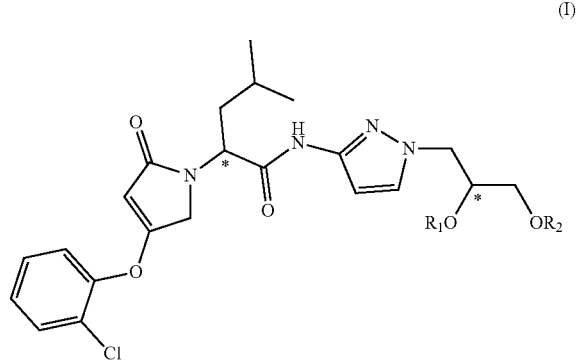

(I)

wherein:
* indicates a chiral center,
$R_1$ is selected from H, —C(O)$R_6$, —C(O)O$R_6$, —C(O)N$R_7R_8$, —S(O)$_m$$R_6$, —S(O)$_m$O$R_6$, or —S(O)$_m$N$R_7R_8$;
$R_2$ is selected from —C(O)$R_3$, —C(O)O$R_3$, —C(O)N$R_4R_5$, —S(O)$_m$O$R_3$, or —S(O)$_m$N$R_4R_5$;
or $R_1$ and $R_2$ are connected to form —CH$R_d$—, —Si$R_dR_e$—, —C(O)—, —S(O)$_{1-2}$—, —P(O)O$R_d$—, or —C$R_dR_e$—C$R_dR_e$—;
$R_3$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl, which is optionally substituted with 1, 2, 3, 4 or 5 R groups;
$R_4$ and $R_5$ are independently selected from H, $C_{1-6}$ alkyl, $C_{2-6}$ alkenyl, $C_{2-6}$ alkynyl, or $C_{1-6}$ haloalkyl; alternatively, $R_4$ and $R_5$ are taken together with the N atom to form 3- to 7-membered heterocyclyl;
$R_6$ is independently selected from H, $C_{1-6}$ alkyl, $C_{2-6}$ alkenyl, $C_{2-6}$ alkynyl, or $C_{1-6}$ haloalkyl;
$R_7$ and $R_8$ are independently selected from H, $C_{1-6}$ alkyl, $C_{2-6}$ alkenyl, $C_{2-6}$ alkynyl, or $C_{1-6}$ haloalkyl; alternatively, $R_7$ and $R_8$ are taken together with the N atom to form 3- to 7-membered heterocyclyl;
R is independently selected from -L-halogen, —L—CN, —L—NO$_2$, —L—O$R_a$, —L—S$R_a$, -13 L—N$R_bR_c$, —L—C(O)O$R_a$, —L—C(O)N$R_bR_c$, —L—S(O)$_m$O$R_a$, —L—S(O)$_m$N$R_bR_c$, $C_{1-6}$ alkyl, $C_{1-6}$ haloalkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, 5- to 10-membered heteroaryl, or a side chain of a natural amino acid;
wherein m is 1 or 2;
$R_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;
$R_b$ and $R_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; alternatively, $R_b$ and $R_c$ are taken together with the N atom to form 3- to 7-membered heterocyclyl;
$R_d$ and $R_e$ are independently selected from H, $C_{1-6}$ alkyl, $C_{2-6}$ alkenyl, $C_{2-6}$ alkynyl, or $C_{1-6}$ haloalkyl; alternatively, $R_d$ and $R_e$ are taken together with the C atom to form =O, =S, $C_{3-7}$ cycloalkyl, or 3- to 7-membered heterocyclyl; and L is selected from a chemical bond, -$C_{1-6}$ alkylene-, -$C_{2-6}$ alkenylene-, or -$C_{2-6}$ alkynylene-.

2. The compound according to claim 1, or an enantiomer, a diastereomer, or a pharmaceutically acceptable salt thereof, wherein the compound is selected from the group consisting of:

(I-1)

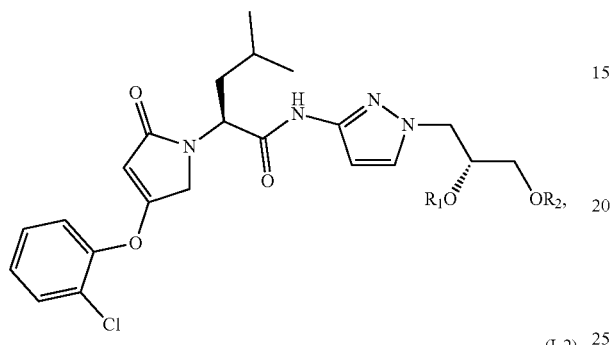

(I-2)

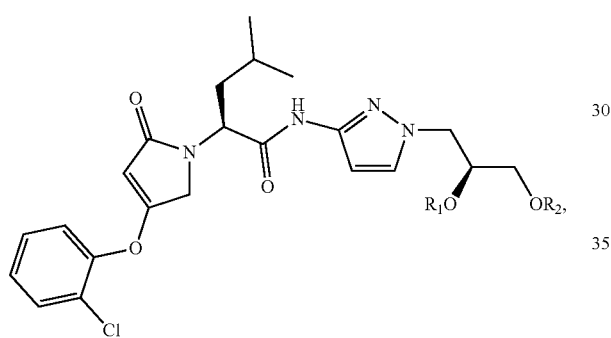

(I-3)

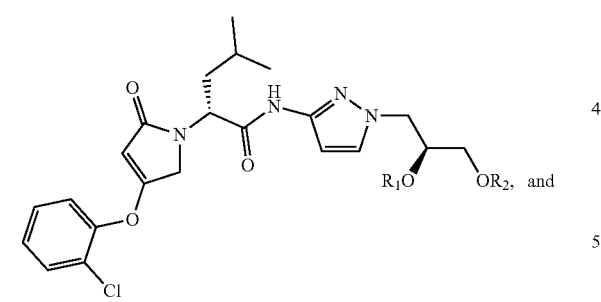

(I-4)

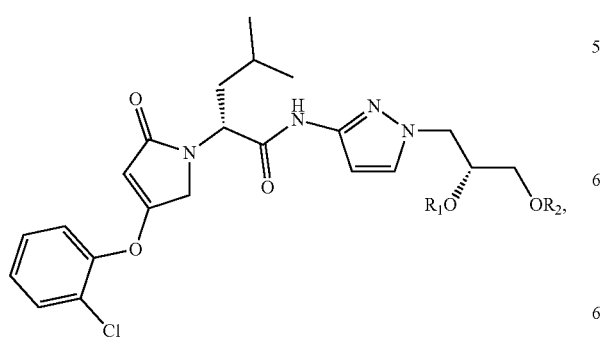

wherein:

$R_1$ is selected from H, —C(O)$R_6$, —C(O)O$R_6$, or —C(O)NR$_7$R$_8$;

$R_2$ is selected from —C(O)$R_3$, —C(O)O$R_3$, or —C(O)NR$_4$R$_5$;

or $R_1$ and $R_2$ are connected to form —SiR$_d$R$_e$—, —C(O)—, —S(O)$_{1-2}$—, —P(O)OR$_d$—, or —CR$_d$R$_e$—CR$_d$R$_e$—;

$R_3$ is independently selected from H, $C_{1-6}$ alkyl, $C_{2-6}$ alkenyl, $C_{2-6}$ alkynyl, or $C_{1-6}$ haloalkyl;

$R_4$ and $R_5$ are independently selected from H, $C_{1-6}$ alkyl, $C_{2-6}$ alkenyl, $C_{2-6}$ alkynyl, or $C_{1-6}$ haloalkyl; alternatively, $R_4$ and $R_5$ are taken together with the N atom to form 3- to 7-membered heterocyclyl;

$R_6$ is independently selected from H, $C_{1-6}$ alkyl, $C_{2-6}$ alkenyl, $C_{2-6}$ alkynyl, or $C_{1-6}$ haloalkyl;

$R_7$ and $R_8$ are independently selected from H, $C_{1-6}$ alkyl, $C_{2-6}$ alkenyl, $C_{2-6}$ alkynyl, or $C_{1-6}$ haloalkyl; alternatively, $R_7$ and $R_8$ are taken together with the N atom to form 3- to 7-membered heterocyclyl; and $R_d$ and $R_e$ are independently selected from H, $C_{1-6}$ alkyl, $C_{2-6}$ alkenyl, $C_{2-6}$ alkynyl, or $C_{1-6}$ haloalkyl; alternatively, $R_d$ and $R_e$ are taken together with the C atom to form =O, =S, $C_{3-7}$ cycloalkyl, or 3- to 7-membered heterocyclyl.

3. The compound according to claim 2, or an enantiomer, a diastereomer, or a pharmaceutically acceptable salt thereof, wherein:

$R_1$ is selected from H, —COMe, or —COOEt; and $R_2$ is selected from —COMe, —COOEt, or —CONHMe;

or $R_1$ and $R_2$ are connected to form —CHMe—, —SiMe$_2$—, —C(O)—, —S(O)$_{1-2}$—, or —P(O)OEt—.

4. The compound according to claim 1, or an enantiomer, a diastereomer, or a pharmaceutically acceptable salt thereof, wherein the compound is selected from the group consisting of:

(II-1)

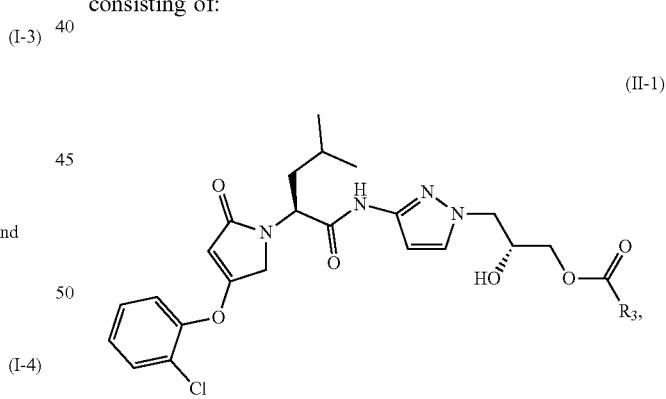

(II-2)

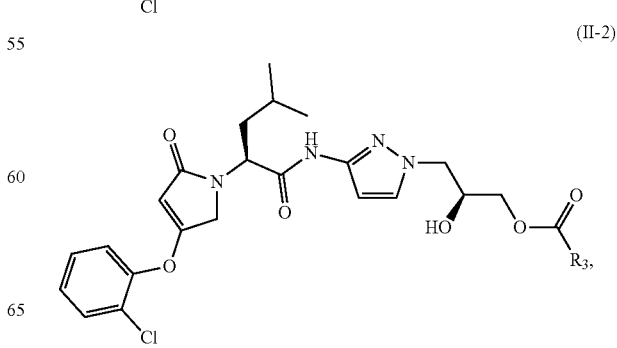

-continued (II-3)

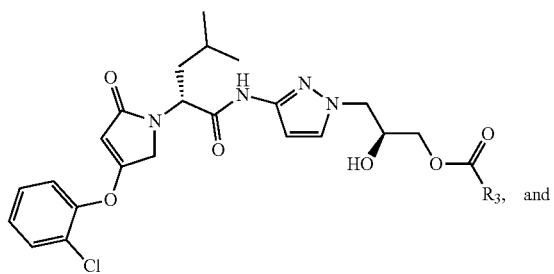

(II-4)

wherein:
- R₃ is selected from $C_{3-7}$ cycloalkyl, 3- to 7-membered heterocyclyl, $C_{6-10}$ aryl, or 5- to 10-membered heteroaryl, which is optionally substituted with 1, 2, 3, 4 or 5 R groups;
- R is independently selected from -L-halogen, —L—CN, —L—NO₂, —L—OR$_a$, —L—SR$_a$, —L—NR$_b$R$_c$, —L—C(O)OR$_a$, —L—C(O)NR$_b$R$_c$, —L—S(O)$_m$OR$_a$, —L—S(O)$_m$NR$_b$R$_c$, $C_{1-6}$ alkyl, $C_{1-6}$ haloalkyl, $C_{2-6}$ alkenyl, or $C_{2-6}$ alkynyl;
- wherein m is 1 or 2;
- R$_a$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl;
- R$_b$ and R$_c$ are independently selected from H, $C_{1-6}$ alkyl, $C_{2-6}$ alkenyl, $C_{2-6}$ alkynyl, $C_{1-6}$ haloalkyl, $C_{3-7}$ cycloalkyl, 3- to 7-membered heterocyclyl, $C_{6-10}$ aryl, or 5- to 10-membered heteroaryl; alternatively, R$_b$ and R$_c$ are taken together with the N atom to form 3- to 7-membered heterocyclyl; and
- L is selected from a chemical bond, —$C_{1-6}$ alkylene-, —$C_{2-6}$ alkenylene-, or —$C_{2-6}$ alkynylene-.

5. The compound according to claim 4, or an enantiomer, a diastereomer, or a pharmaceutically acceptable salt thereof, wherein
- R₃ is selected from $C_{6-10}$ aryl or 5- to 6-membered heteroaryl, which is optionally substituted with 1, 2, 3, 4 or 5 R groups;
- R is independently selected from halogen, —CN, —NO₂, —OH, —SH, —NH₂, —C(O)OH, —C(O)NH₂, —S(O)$_m$OH, —S(O)$_m$NH₂, $C_{1-6}$ alkyl, $C_{1-6}$ haloalkyl, $C_{2-6}$ alkenyl, or $C_{2-6}$ alkynyl; and
- wherein m is 1 or 2.

6. The compound according to claim 4, or an enantiomer, a diastereomer, or a pharmaceutically acceptable salt thereof, wherein
- R₃ is selected from phenyl, naphthyl, pyrrolyl, furyl, thienyl, imidazolyl, pyrazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, triazinyl, or tetrazinyl, which is optionally substituted with 1, 2, 3, 4 or 5 R groups;
- R is independently selected from halogen, —CN, —NO₂, —OH, —SH, —NH₂, —C(O)OH, —C(O)NH₂, —S(O)$_m$OH, or —S(O)$_m$NH₂; and
- wherein m is 1 or 2.

7. The compound according to claim 4, or an enantiomer, a diastereomer, or a pharmaceutically acceptable salt thereof, wherein
- R₃ is selected from phenyl, pyridyl, pyridazinyl, pyrimidinyl, pyrazinyl, triazinyl, or tetrazinyl, which is optionally substituted with 1, 2 or 3 R groups; and
- R is independently selected from halogen, —CN, —NO₂, —OH, —SH, or —NH₂.

8. The compound according to claim 1, or an enantiomer, a diastereomer, or a pharmaceutically acceptable salt thereof, wherein the compound is selected from the group consisting of:

(III-1)

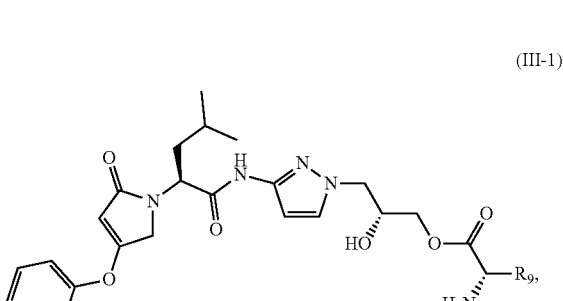

(III-2)

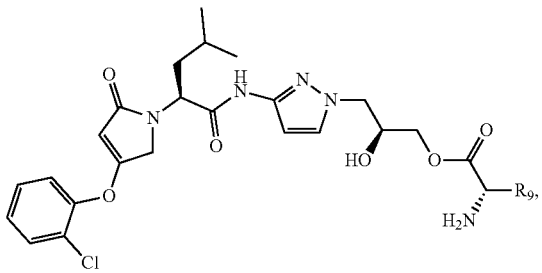

(III-3)

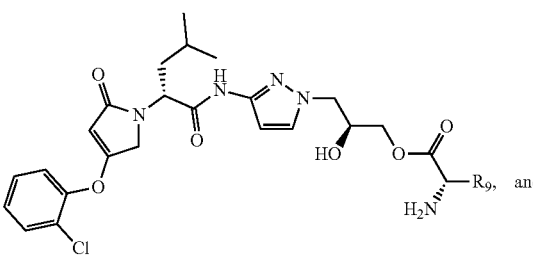

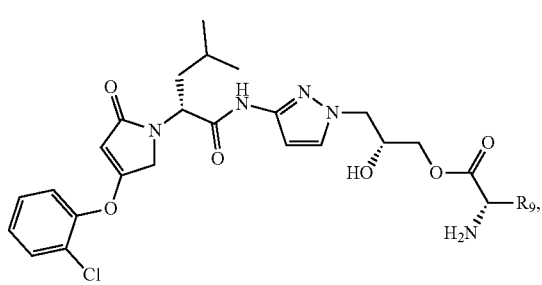

(III-4)

wherein:

R₉ is selected from H, -L-halogen, —L—CN, —L—NO₂, —L—OR_a, —L—SR_a, —L—NR_bR_c, —L—C(O)OR_a, —L—C(O)NR_bR_c, —L—S(O)_mOR_a, —L—S(O)_mNR_bR_c, C_{1-6} alkyl, C_{2-6} alkenyl, C_{2-6} alkynyl, C_{1-6} haloalkyl, C_{3-7} cycloalkyl, 3- to 7-membered heterocyclyl, C_{6-10} aryl, 5- to 10-membered heteroaryl, or a side chain of a natural amino acid;

wherein m is 1 or 2;

R_a is independently selected from H, C_{1-6} alkyl, C_{2-6} alkenyl, C_{2-6} alkynyl, C_{1-6} haloalkyl, C_{3-7} cycloalkyl, 3- to 7-membered heterocyclyl, C_{6-10} aryl, or 5- to 10-membered heteroaryl;

R_b and R_c are independently selected from H, C_{1-6} alkyl, C_{2-6} alkenyl, C_{2-6} alkynyl, C_{1-6} haloalkyl, C_{3-7} cycloalkyl, 3- to 7-membered heterocyclyl, C_{6-10} aryl, or 5- to 10-membered heteroaryl; alternatively, R_b and R_c are taken together with the N atom to form 3- to 7-membered heterocyclyl; and L is selected from a chemical bond, —C_{1-6} alkylene-, —C_{2-6} alkenylene-, or —C_{2-6} alkynylene-.

9. The compound according to claim 8, or an enantiomer, a diastereomer, or a pharmaceutically acceptable salt thereof, wherein R₉ is selected from H, C_{1-6} alkyl, C_{2-6} alkenyl, C_{2-6} alkynyl, C_{1-6} haloalkyl, C_{3-7} cycloalkyl, 3- to 7-membered heterocyclyl, C_{6-10} aryl, 5- to 10-membered heteroaryl, or a side chain of a natural amino acid.

10. The compound according to claim 8, or an enantiomer, a diastereomer, or a pharmaceutically acceptable salt thereof, wherein R₉ is the side chain of natural amino acids selected from the group consisting of glycine, alanine, valine, leucine, isoleucine, phenylalanine, tryptophan, tyrosine, aspartic acid, asparagine, glutamic acid, lysine, glutamine, methionine, serine, threonine, cysteine, histidine, and arginine.

11. The compound according to claim 8, or an enantiomer, a diastereomer, or a pharmaceutically acceptable salt thereof, wherein R₉ is alanine side chain (Me) or valine side chain (iPr).

12. The compound according to claim 1, or an enantiomer, a diastereomer, or a pharmaceutically acceptable salt thereof, wherein the compound is selected from the group consisting of:

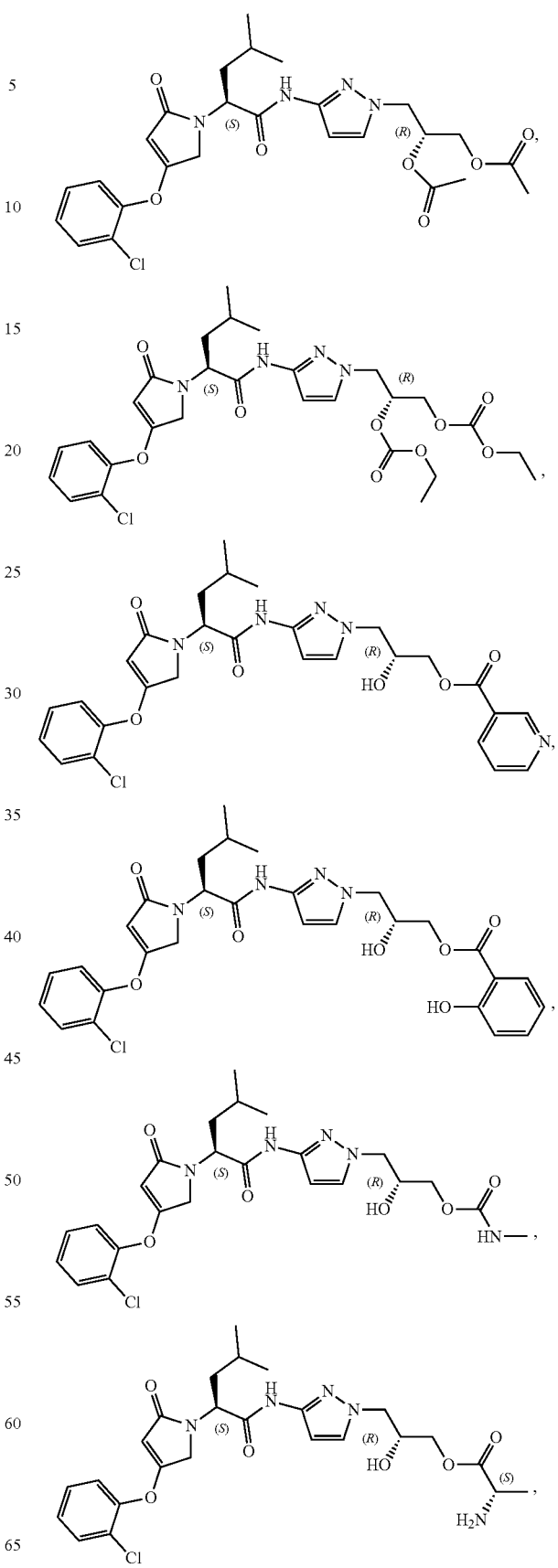

-continued

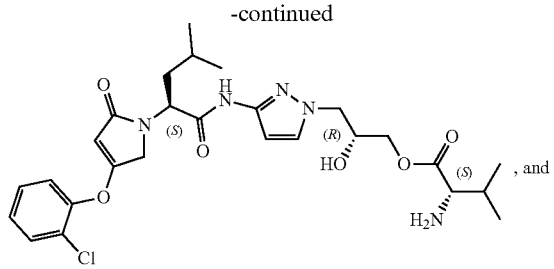

, and

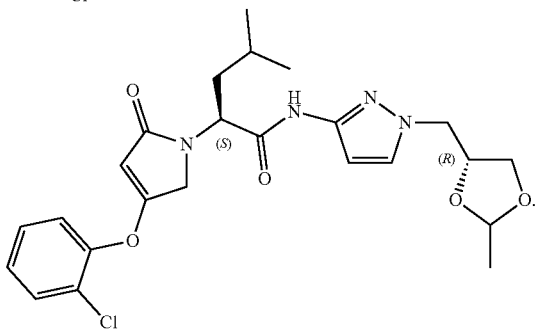

14. A pharmaceutical composition, comprising the compound of claim 1, or an enantiomer, a diastereoisomer, or a pharmaceutically acceptable salt thereof; and optionally one or more pharmaceutically acceptable excipients.

15. A compound, which is:

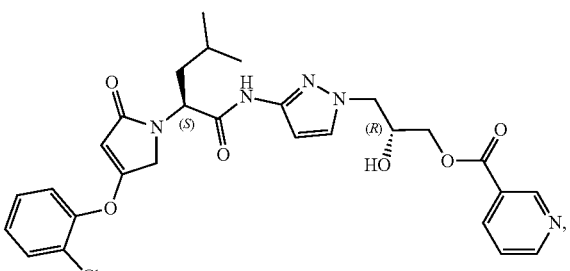

or a pharmaceutically acceptable salt thereof.

13. The compound according to claim 12, or an enantiomer, a diastereomer, or a pharmaceutically acceptable salt thereof, wherein the pharmaceutically acceptable salt of the compound is:

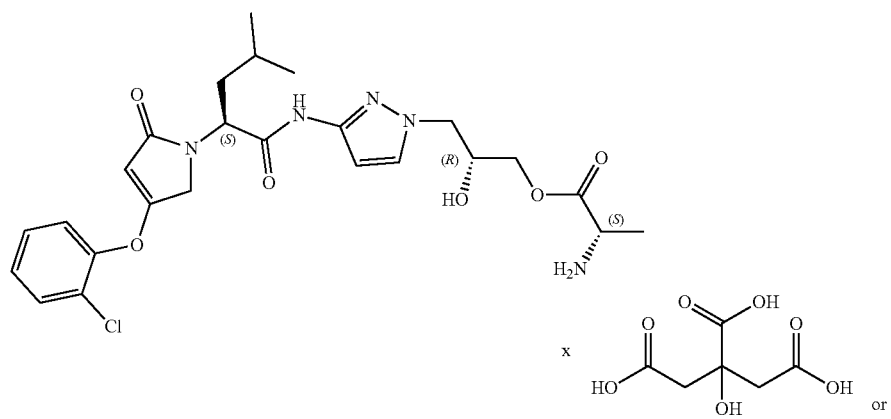

or

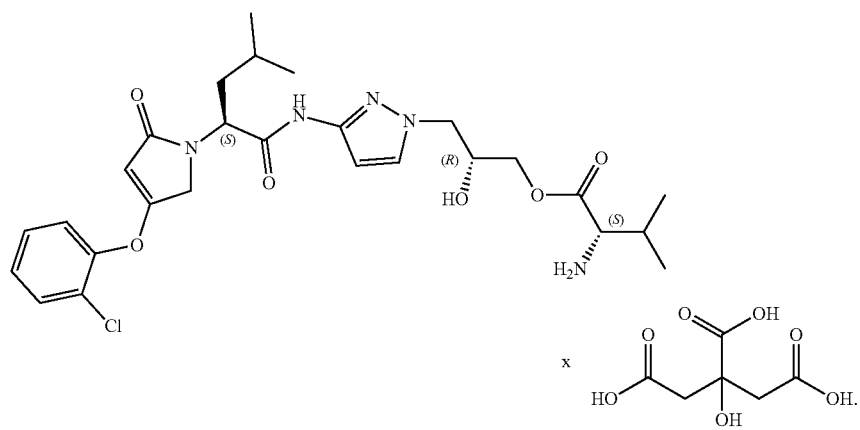

16. The compound of claim 15, which is:
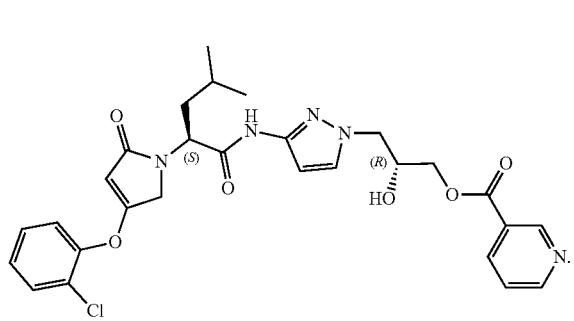
17. A compound, which is:
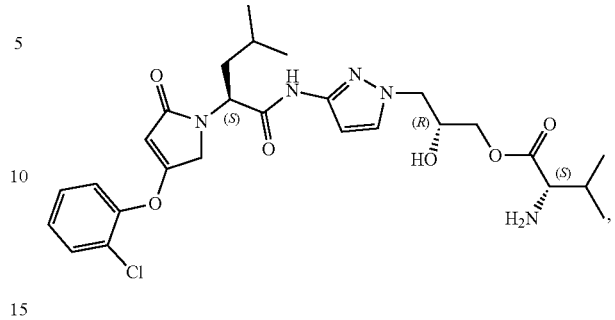
or a pharmaceutically acceptable salt thereof.
18. The compound of claim 17, which is:
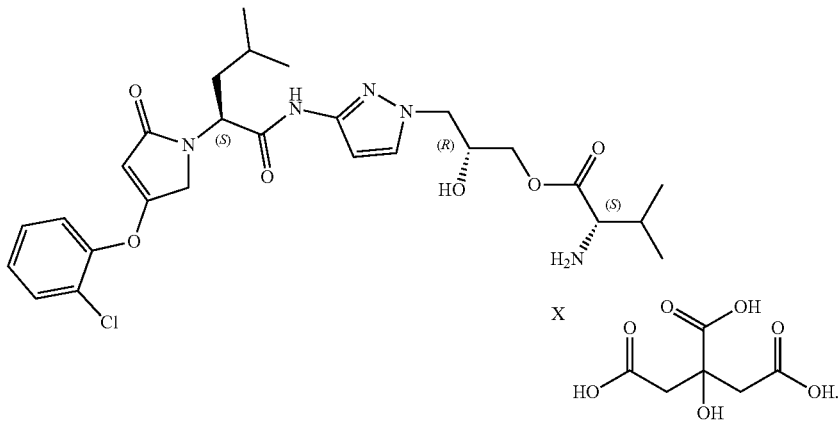
19. The compound of claim 17, which is:
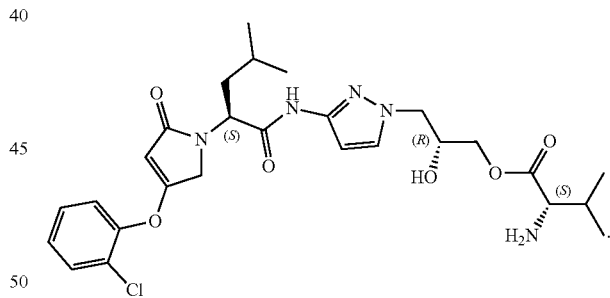
* * * * *

UNITED STATES PATENT AND TRADEMARK OFFICE
CERTIFICATE OF CORRECTION

PATENT NO. : 12,054,477 B2
APPLICATION NO. : 18/333459
DATED : August 6, 2024
INVENTOR(S) : Tang et al.

It is certified that error appears in the above-identified patent and that said Letters Patent is hereby corrected as shown below:

In the Specification

In Column 3, Line 1, replace the term "$R_7$ and $R_5$" with "$R_7$ and $R_8$".

In Column 5, Line 5, replace the term "$C_{24}$" with "$C_{2-4}$".

In Column 5, Line 19, replace the term "$C_{24}$" with "$C_{2-4}$".

In Column 5, Line 52, replace the term "$C_{24}$" with "$C_{2-4}$".

In Column 5, Line 67, replace the term "$C_{24}$" with "$C_{2-4}$".

In Column 12, Line 45, replace the term "$R_7$ and $R_5$" with "$R_7$ and $R_8$".

In Column 12, Line 63, replace the term "$C_{1.}6$" with "$C_{1-6}$".

In Column 13, Line 4, replace the term "$C_{3-}7$" with "$C_{3-7}$".

In Column 14, Line 52, replace the term "$C_{3-}7$" with "$C_{3-7}$".

In Column 15, Line 67, replace the term "$C_{1.}6$" with "$C_{1-6}$".

In Column 18, Line 11, replace the term "$C_{1.}6$" with "$C_{1-6}$".

In Column 35, Line 63, replace the term "DMVF" with "DMF".

In Column 41, Line 9, replace the term "$K_2TIPO_4$" with "$K_2HPO_4$".

In Column 41, Line 18, replace the term "50 mM, 990 ACN" with "50 µM, 99% ACN".

Signed and Sealed this
Fifteenth Day of October, 2024

*Katherine Kelly Vidal*
Katherine Kelly Vidal
*Director of the United States Patent and Trademark Office*

CERTIFICATE OF CORRECTION (continued)
U.S. Pat. No. 12,054,477 B2

In Column 42, Line 16, replace the term "1.7 m" with "1.7μm".

In Column 42, Line 25 (Table 6), replace the term "Time (min) Point" with "Time Point (min)".

In Column 42, Line 64, replace the term "10.0 M" with "10.0μM".

In Column 43, Line 8, replace the term "30.0 M" with "30.0μM".

In Column 45, Line 55, replace the term "HIMS5552" with "HMS5552".

In Column 45, Line 57, replace the term "HMIN/S5552" with "HMS5552".

In Column 45, Line 62, replace the term "HIMS5552" with "HMS5552".

In the Claims

In Column 48, Line 48 (Claim 1), replace the term "-13 L-$NR_bR_c$" with "-L-$NR_bR_c$".

In Column 48, Line 66 (Claim 1), replace the term "$R_d$ and $R_c$" with "$R_d$ and $R_e$".

In Column 50, Line 28 (Claim 3), replace the term "claim 2" with "claim 1".